United States Patent
Sell et al.

(10) Patent No.: US 9,968,558 B2
(45) Date of Patent: May 15, 2018

(54) FABRICATION OF HYDROGEL MICROSPHERE DELIVERY VEHICLES THROUGH ELECTROSPRAYING AND TIMED GELATION

(71) Applicant: Saint Louis University, St. Louis, MO (US)

(72) Inventors: Scott Sell, St. Louis, MO (US); Era Jain, St. Louis, MO (US); Silviya Zustiak, St. Louis, MO (US); Kayla May Scott, Richmond, VA (US); Saahil Sheth, St. Peters, MO (US)

(73) Assignee: Saint Louis University, St. Louis, MO (US)

( * ) Notice: Subject to any disclaimer, the term of this patent is extended or adjusted under 35 U.S.C. 154(b) by 0 days. days.

(21) Appl. No.: 15/075,294

(22) Filed: Mar. 21, 2016

(65) Prior Publication Data

US 2016/0271064 A1  Sep. 22, 2016

Related U.S. Application Data

(60) Provisional application No. 62/136,089, filed on Mar. 20, 2015.

(51) Int. Cl.
| | |
|---|---|
| *A61K 38/47* | (2006.01) |
| *A61K 9/16* | (2006.01) |
| *A61K 38/38* | (2006.01) |
| *A61K 35/16* | (2015.01) |
| *A61K 39/395* | (2006.01) |
| *A61K 38/48* | (2006.01) |

(52) U.S. Cl.
CPC .......... *A61K 9/1682* (2013.01); *A61K 9/1641* (2013.01); *A61K 35/16* (2013.01); *A61K 38/385* (2013.01); *A61K 38/47* (2013.01); *A61K 38/4833* (2013.01); *A61K 39/395* (2013.01); *C12Y 302/01017* (2013.01); *C12Y 304/21005* (2013.01)

(58) Field of Classification Search
CPC ...... A61K 35/16; A61K 38/385; A61K 38/47; A61K 38/4833; A61K 39/395; A61K 9/1641; A61K 9/1682; C12Y 302/01017; C12Y 304/21005
See application file for complete search history.

(56) References Cited

U.S. PATENT DOCUMENTS

| | | | | |
|---|---|---|---|---|
| 6,365,656 B1 * | 4/2002 | Green | ............ | A61K 8/0241 424/70.1 |
| 2008/0241267 A1 * | 10/2008 | Verrijk | ............ | A61K 9/0019 424/499 |
| 2010/0291191 A1 * | 11/2010 | Shoichet | ............ | A61K 9/0024 424/450 |

OTHER PUBLICATIONS

Polymerization [online] retrieved on Jan. 4, 2017 from: https://www.britannica.com/print/article/468745; 3 pages.*
Zustiak et al. (Biomacromolecules 2010;11:1348-1357).*
Bock et al. (Polymers 2011;3:131-149).*
Zarrabi et al. (Roznov pod Rodhostem NONOCON 2009; 8 pages).*
Young et al. (Biotechnology and Bioengineering 2012;109:1561-1570).*

(Continued)

*Primary Examiner* — Ernst V Arnold
(74) *Attorney, Agent, or Firm* — Stinson Leonard Street LLC

(57) ABSTRACT

Disclosed are processes for making hydrogel microspheres. More particularly, the present disclosure is directed to processes for making hydrogel microspheres by electrospraying.

17 Claims, 16 Drawing Sheets

(56) References Cited

OTHER PUBLICATIONS

Ji eta l. (Biomaterials 2006;27:3782-3792).*
Kessel et al. (Transcather Embolization and Therapy 2010; p. 34) (Year: 2010).*
Kim et al. (Microspheres for Drug Delivery Chapter 2 of: BioMEMS and Biomedical Nanotechnology 2006;vol. 1: pp. 19-50) (Year: 2006).*
Bedouet et al., Intra-articular fate of degradable poly(ethyleneglycol)-hydrogel microspheres as carriers for sustained drug delivery, International Journal of Pharmaceutics, vol. 456, pp. 536-544, 2013.
Franssen et al., A novel preparation method for polymeric microparticles without the use of organic solvents, International Journal of Pharmaceutics, vol. 168, pp. 1-7, 1998.
King et al., Facile Formation of Dynamic Hydrogel Microspheres for Triggered Growth Factor Delivery, Acta Biomater., 2011, vol. 7, No. 3, pp. 975-985.
Mahou et al., Alginate-Poly(ethylene glycol) Hybrid Microspheres for Primary Cell Microencapsulation, Materials ISSN 1996-1944, vol. 7, pp. 275-286, 2014.
Nichols et al., Factors affecting size and swelling of poly(ethylene glycol) microspheres formed in aqueous sodium sulfate solutions without surfactants, Biomaterials, vol. 30, pp. 5283-5291, 2009.
Parlato et al., Adaptable Poly(ethylene glycol) Microspheres Capable of Mixed-mode Degradation, Acta Biomater., 2013., vol. 9, No. 12, pp. 9270-9280.
Pradhan et al., Duel-Phase, Surface Tension-Based Fabrication Method for Generation of Tumor Millibeads, American Chemical Society, 2014, pp. 3817-3825.
Rossow et al., Controlled Synthesis of Cell-Laden Microgels by Radical-Free Gelation in droplet Microfluidics, Journal of the American Chemical Society, 2012, pp. 4983-4989.
Song et al., Monodisperse w/w/w Double Emulsion Induced by Phase Separation, American Chemical Society, 2012, pp. 12054-12059.

* cited by examiner

Storage at -80° for 24 hr    Rehydration: 24h

Storage at -20° for 24 hr    Rehydration: 24h

Lyophilized Microspheres    Rehydration: 24h

FABRICATION OF HYDROGEL MICROSPHERE DELIVERY VEHICLES THROUGH ELECTROSPRAYING AND TIMED GELATION

CROSS-REFERENCE TO RELATED APPLICATIONS

This application claims the benefit to U.S. Provisional Application Ser. No. 62/136,089, filed Mar. 20, 2015, which is incorporated herein by reference in its entirety.

BACKGROUND

The present disclosure relates generally to processes for making hydrogel microspheres. More particularly, the present disclosure is directed to processes for making hydrogel microspheres by electrospraying and to processes for making hydrogel microspheres by electrospraying using a solution having a timed gelation.

Hydrogel microspheres of less than 200 µm are powerful tools that have a multitude of applications in the areas of drug delivery, tissue engineering, and biosensors. Hydrogels are a preferred choice because of their tissue-like properties, high water content, ease of fabrication (Lee and Mooney 2001, Hoare and Kohane 2008) and tunable chemical, mechanical and biological characteristics.

Hydrogels composed of polyethylene glycol (PEG) are used often for many biological applications because of its inertness, resistance to protein adsorption, excellent biocompatibility and versatility of PEG macromer chemistry. For encapsulation and delivery of sensitive biological components such as drug, cells, protein, etc., microspheres are a preferred configuration. Encapsulation of bioactive molecules in the semi-permeable membrane formed by the microsphere components not only protects their activity but also simultaneously permits control over their release. Additionally, microspheres can be tailored to be injectable for site-specific delivery and the sustained release of a number of biomolecules.

Numerous methods have been proposed to generate hydrogel microspheres. In general, formation of hydrogel microspheres requires a combination of two mechanisms: droplet generation and a gelation mechanism to with-hold the formed droplet. Droplet generation for making hydrogel microspheres of controlled size and shape can be done using methods such as emulsification precipitation or dispersion and microfluidic channels. In the case of solution dispersion methods such as emulsification, or suspension methods, droplets are generated by mixing immiscible liquids and generating a dispersed phase using various mixing methods such as vortexing, sonication or micronization. However, the high shear stress induced by vortexing, or other mechanical break up methods is harmful for biological applications such as cell or protein encapsulation. Moreover, most of the dispersion-based methods involve the use of either organic solvent or surfactants. Although methods such as microfluidic devices offer a lot of control over process parameters and fabrication characteristics, the devices are very complex in design, and thus, limit widespread applications.

Once a fine dispersion of precursor solution is obtained by any of the above methods, the particles can be cross-linked via covalent and non-covalent crosslinks using a variety of methods. In particular, crosslinking in PEG hydrogel microspheres can be done by chain growth mode based on free radical polymerization, step growth based on conjugate addition, or mixed mode (a combination of chain and step growth). Most of the chemical crosslinking methods or agents employed are harmful to biological molecules which limits their biological application.

It has also been shown that an aqueous based phase separation method may be used to obtain PEG hydrogel microspheres via mixed mode polymerization. Although such a method does not involve use of an organic solvent, an inherent disadvantage is the use of a photointiator and UV light for crosslinking, which are known to be harmful for biological entities and drug stability.

Accordingly, there is a need for a mild process for preparing hydrogel microspheres for bioactive molecule and cell encapsulation. As provided herein, the present disclosure provides a mild process for making hydrogel microspheres by electrospraying to generate fine droplets and subsequently utilizing a controlled, timed gelation for hydrogel formation.

BRIEF DESCRIPTION

In one aspect, the present disclosure is directed to a method of preparing hydrogel microspheres. The method comprises: preparing a gel precursor solution, wherein the gel precursor solution comprises a polymer and a crosslinker; electrospraying the gel precursor solution; collecting microspheres; and polymerizing the collected microspheres to form hydrogel microspheres.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3A is a digital image depicting droplet formation in the dripping mode at 5 kV applied voltage. FIG. 3B is a digital image depicting Taylor cone formation during electrospraying at an applied voltage of 10 kV.

FIG. 4A depicts mean microsphere diameter of microspheres when the applied voltage was increased from 5 kV to 25 kV. FIGS. 4B-4D are histograms depicting representative single runs demonstrating microsphere polydispersity are shown at applied voltages of 5 kV (FIG. 4B), 10 kV (FIG. 4C), and 25 kV (FIG. 4D). Average CV values from triplicate runs at indicated parameters were 16%, 32%, and 36%, respectively. All runs were carried out at 1 ml hr$^{-1}$ flow rate, TTCD of 114 mm and 30 G needle. *Indicates statistical significance (ANOVA, p≤0.05). FIG. 4E depicts the effect of increasing voltage from 5 kV to 15 kV on cell viability.

FIG. 5A depicts the size distribution of microspheres when flow rate was increased from 1 ml hr$^{-1}$ to 10 ml hr$^{-1}$. FIGS. 5B-5D are histograms depicting representative runs demonstrating microsphere polydispersity shown at flow rates of 1 ml hr$^{-1}$ (FIG. 5B), 7.5 ml 5C), and 10 ml hr$^{-1}$ (FIG. 5D). The average CV values from triplicate runs at indicated parameters were 32%, 32%, and 23%, respectively. All the runs were carried out at 10 kV, TTCD of 114 mm and buffer pH 7.4 using 30 G needle. *Indicates statistical significance (ANOVA p<0.05) and NS indicates no statistical significance. FIG. 5E depicts the effect of increasing flow rate from 1 ml hr$^{-1}$ to 5 ml hr$^{-1}$ on cell viability.

FIG. 6A depicts the size distribution of microspheres when TTCD was increased from 38 mm to 216 mm FIGS. 6B-6E are histograms depicting representative runs demonstrating microsphere polydispersity are shown at TTCD of: 38 mm (FIG. 6B), 64 mm (FIG. 6C), 114 (FIG. 6D), and 216 mm (FIG. 6E). Average CV values from triplicate runs at the indicated parameters were 27%, 26%, 32%, and 17%, respectively. All runs were carried out at 10 kV applied voltage, flow rate of 1 ml hr$^{-1}$ and solution pH 7.4 using 30 G needle. *Indicates statistical significance (ANOVA p<0.05) and NS indicates no statistical significance.

FIG. 7A depicts the size distribution of microspheres when needle gauge was changed from 30 to 18 G. FIGS. 7B-7D are histograms depicting representative runs demonstrating microsphere polydispersity are presented at needle gauge of: 30 G (FIG. 7B), 21 G (FIG. 7C), and 18 G (FIG. 7D). Average CV values from triplicate runs at indicated parameters were 32%, 41%, and 38%, respectively. All the runs were carried out at 10 kV applied voltage, flow rate of 1 ml hr$^{-1}$ and solution pH 7.4 and TTCD of 114 mm *Indicates statistical significance (ANOVA p<0.05) and NS indicates no statistical significance. FIG. 7E depicts the effect of increasing needle gauge on cell viability.

FIG. 9A depicts microspheres that were frozen by slow freezing at −80° C. for 24 h and re-swollen for 24 h. FIG. 9B depicts microspheres that were frozen by slow freezing at −20° C. for 24 h and re-swollen for 24 h. FIG. 9C depicts microspheres that were lyophilized and re-swollen for 24 h.

Figure 1:
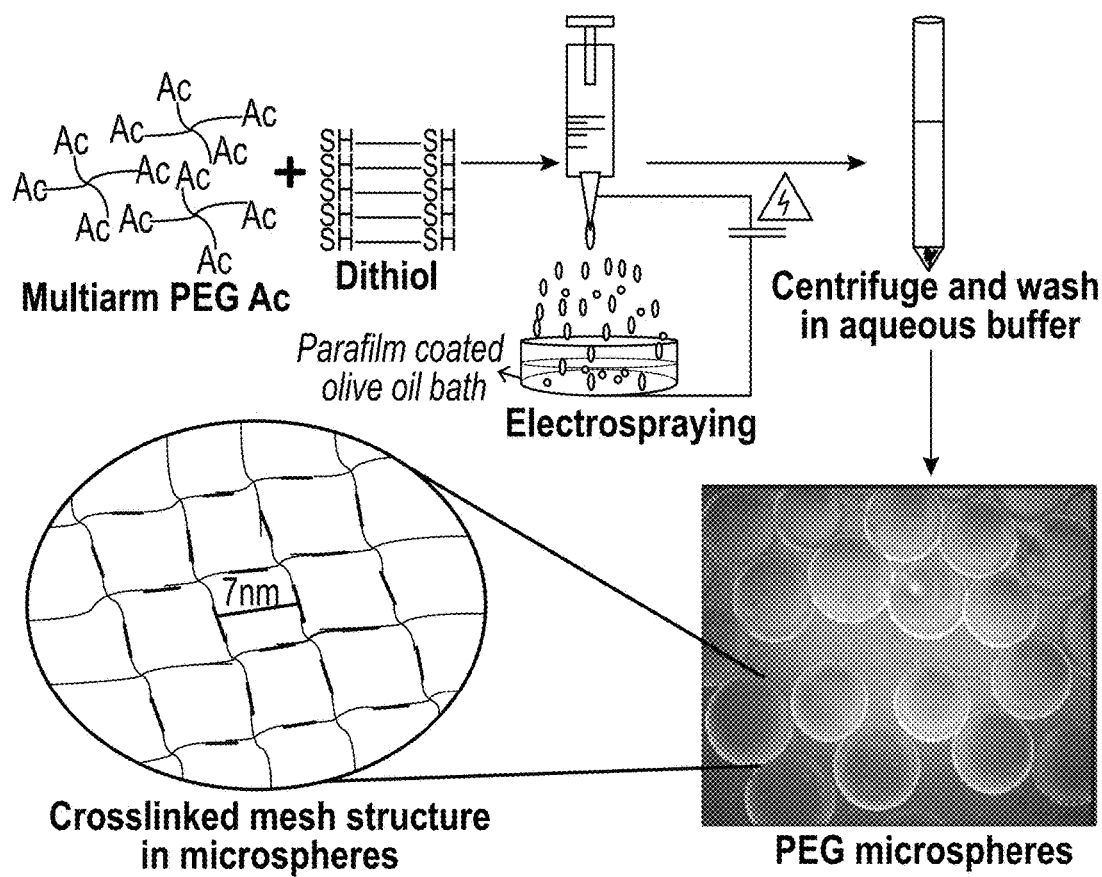
FIG. 1 is a diagrammatic representation depicting the process used for making PEG hydrogel microspheres. The acrylate group (Ac) in PEG reacts with the thiol group of the dithiothreitol (DTT) via Michael's type addition mechanism to form a hydrogel network. The hydrogel microspheres are electrosprayed before the gelation reaction is completed and collected in an olive oil bath. Post gelation, the PEG hydrogel microspheres are collected by centrifugation and washed with an aqueous buffer to remove residual oil. An image representing the resulting PEG hydrogel microspheres after washing is depicted with a schematic illustrating the crosslinked mesh structure in a hydrogel microsphere.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

In accordance with the present disclosure, methods for preparing hydrogel microspheres are described. The hydrogel microsphere fabrication method used here provides tunable design characteristics such as degradation rates, mesh size, protein release kinetics, and microsphere size. The microspheres are effective as controlled drug delivery vehicles as they provide high encapsulation efficiency as well as maintenance of the biological activity of the proteins or cells over an extended period of time. The micron-scale nature of the microspheres allows them to serve as minimally invasive delivery vehicles in a number of medical applications including, for example, knee osteoarthritis, dermal repair, enzyme replacement therapy, etc. The hydrogel microspheres of the present disclosure can also be used for cell encapsulation and preservation, as well as the encapsulation and delivery of countless other biologics for countless applications (e.g. controlled release).

It is believed that the methods described herein include the first use of electrospraying and timed gelation chemistry for making hydrogel microspheres. Traditionally, hydrogels/microspheres are fabricated using potentially harsh chemistry, UV light crosslinking, oil emulsion with sonication baths, or microfluidics; methods which can denature proteins and damage cells. The electrospraying method described here uses a solution having timed gelation and the application of an electric field to create uniform microspheres of varying sizes and it is not harmful to proteins and cells.

In one aspect, the present disclosure is directed to a method of preparing hydrogel microspheres. The method includes preparing a gel precursor solution, wherein the gel precursor solution comprises a polymer and a crosslinker; electrospraying the gel precursor solution; collecting microspheres; and polymerizing the collected microspheres to form hydrogel microspheres. The polymer and crosslinker form a covalent bond in a controlled fashion through Michael type addition chemistry. Michael type addition chemistry allows for the controlled, time gelation of the electrosprayed microspheres. The time to gelation can be controlled by altering the precursor solution pH, the concentration of the polymer, the concentration of the crosslinker, the molecular weight of the polymer, the molecular weight of the crosslinker, the chemical structure of the polymer, the chemical structure of the crosslinker, and combinations thereof.

Suitable polymer concentrations of the gel precursor solution can be about 3% w/v to about 40% w/v. Suitable pH of the gel precursor solution can be about 6.0 to about 8.5. The applied voltage can be from about 1 kV to about 30 kV. Suitable flow rates can be from about 0.5 ml hr$^{-1}$ to about 20 ml hr$^{-1}$. Suitable tip to collector distance can be about 25 millimeters to about 300 millimeters. Suitable needle gauges can be about 30 G to about 14 G.

The average microsphere size can be from about 50 μm to about 700 μm. Particularly suitable microsphere size can be from about 50 μm to about 250 μm. Microsphere size can be determined by imaging microspheres using a microscope and analyzing microscopic images using software such as, for example, IMAGE J. Microsphere size distribution can be obtained based on a microsphere count from one or more replicate runs.

The hydrogel microsphere degradation rate can be from about 2 hours to about 32 days. The degradation times can be modified based on the gelation pH, type of crosslinker, type of PEG acrylate, and incubation medium. Increasing the gelation pH from neutral to more basic can decrease the degradation time. Using ester based crosslinkers or thiols with pKa of 8 to 8.8 decrease the degradation time. Using low molecular weight PEG and multiarm PEG acrylate decrease the degradation time. Decreasing gelation pH to 7 can increase degradation time. Using crosslinkers of pKa>9 can increase degradation time. Using high molecular weight multiarm PEG acrylate can increase degradation time.

The method can further include collecting the microspheres in a collection medium. The collection medium can be any liquid in which the gel precursor solution is immiscible. Particularly suitable collection media can be mineral oil, olive oil, silicon oil, sunflower oil, canola oil, vegetable oil, palm oil, soybean oil, corn oil, rice bran oil, safflower oil, peanut oil, sesame oil, argan oil, grape seed oil, an aqueous dextran solution, and combinations thereof.

The gel precursor solution includes a polymer. Suitable polymers can be multiarm polymers and linear polymers. Particularly suitable polymers can be polymers with end groups including acrylates (Ac), methyacryaltes (MA), vinyl sulfones (VS), unsaturated double bond moieties, and combinations thereof. Particularly suitable polymers can be polyethylene glycol (PEG), poly(glycolic acid) (PGA), poly(L-lactic acid) (PLA), poly(lactide-co-glycolide) (PLGA), poly(L-lactide) (PLLA), poly(D,L-lactide) (p(DLLA)), poly(ethylene glycol)1-co-poly(L-lactide) (PEG-PLLA), poly(ε-caprolactone) (PCL), poly(L-lactide-co-ε-caprolactone) (P(LLA-CL)), poly(ε-caprolactone-co-ethyl ethylene phosphate (P(CL-EEP)), poly(ethylene-co-vinyl alcohol), poly(ethylenimine), polymethylmethacrylate (PMMA), hyaluronic acid, chitosan, pluronics, polyacrylamide, poly(vinyl alcohol) (PVA), polyhydroxyethylmethacrylate (poly-HEMA), and combinations thereof. Particularly suitable unsaturated double bond terminated polyethylene glycols can be linear, 3-arm, 4-arm, 6-arm, and 8-arm unsaturated double bond terminated polyethylene glycols. Table 1 summarizes the physical properties of hydrogels made at different pH with various PEG multiacrylates and various dithiol croslinkers.

TABLE 1

Physical Properties of Exemplary Hydrogels.

| Hydrogel System | Reaction pH | Swelling Ratio ($M_{sw}/M_d$) | Gelation Time (s) | Mesh Size (nm) | Storage Modulus |
|---|---|---|---|---|---|
| PEG (4A)-GDT | 7 | 17.93 ± 2.35 | 153 ± 4.24 | 9.71 ± 0.43 | 3553 ± 533 |
| PEG (4A)-GDMA | 7 | 18.37 ± 2.55 | 199 ± 36 | 11.33 ± 0.12 | 5838.96 ± 431 |
| PEG (4A)-GDMP | 7 | 16.72 ± 2.33 | 1400 ± 139 | 10.83 ± 0.16 | 2764.79 ± 735 |
| PEG (4A)-PEG DD-1 | 7 | 20.91 ± 1.24 | 365 ± 77 | 13.76 ± 0.17 | 4236.06 ± 973 |
| PEG (4A)-PEG DD-2 | 7 | 18.36 ± 2.57 | 1800 ± 117 | 12.25 ± 0.72 | 4454.36 ± 412 |
| PEG (4A)-EDDT | 7 | 16.27 ± 0.70 | 1419 ± 27 | 10.63 ± 0.28 | 7376.99 ± 1556 |
| PEG (4A)-TEGDT | 7 | 14.84 ± 0.47 | 1736 ± 113 | 10.40 ± 0.04 | 9818.64 ± 318 |
| PEG-(4A)- | 7 | 21.98 ± 0.36 | 2020 ± 197 | 13.81 ± 0.10 | 4403.24 ± 1360 |

TABLE 1-continued

Physical Properties of Exemplary Hydrogels.

| Hydrogel System | Reaction pH | Swelling Ratio ($M_{sw}/M_d$) | Gelation Time (s) | Mesh Size (nm) | Storage Modulus |
|---|---|---|---|---|---|
| PEGdiSH PEG (4A)DTT | 7 | 12.41 ± 0.91 | 1673 ± 46 | 9.48 ± 0.29 | 12403.80 ± 1246 |
| PEG (4A)-DTBA | 7 | 16.57 ± 1.78 | 541 ± 12 | 10.83 ± 0.23 | 6992.45 ± 697 |
| PEG (4A)-DTT | 8.5 | 17.88 ± 0.768 | 121 ± 36.34 | 11.03 ± 0.73 | 7593.79 ± 1493 |
| PEG (6A)-DTT | 7 | 11.41 ± 0.84 | 889 ± 78.48 | 10.62 ± 0.61 | nd |
| PEG (8A)-DTT | 7 | 10.02 ± 0.82 | 647 ± 66.46 | 9.41 ± 0.11 | 16944.2 ± 2379 |

The gel precursor solution further includes a crosslinker. Suitable crosslinkers can be thiol-terminated polymers, small molecules, cysteine-terminated oligopeptides, cysteine-terminated polypeptides, and combinations thereof. Particularly suitable crosslinkers can be multithiol crosslinkers. Particularly suitable multithiol crosslinkers can be, for example, dithiothreitol (DTT), polyethylene glycol thiols (including for example, 3-arm, 4-arm, 6-arm, or 8-arm), polyethylene glycol thioglacolate (including for example, linear, 3-arm, 4-arm, 6-arm, or 8-arm), polyethylene glycol thiopropionate (including for example, 3-arm, 4-arm, 6-arm, or 8-arm), glycol dimercaptoacetate (GDMA), glycol di(3-mercaptopropionate) (GDMP), glyceryl dithioglycolate (GDT), tris [2-(3-mercaptopropionyloxy)ethyl]isocyanurate, pentaerythritol tetra-3-mercaptopropionate, ethoxilated-trimethylolpropan tri-3-mercaptopropionate, 2,2'-(Ethylenedioxy) diethanethiol (EDDT), Tetraethylene glycol dithiol (TEGDT), (S)-2 aminobutane 1,4 dithiol (DTBA) and other thiol terminated molecules and cysteine containing oligo- and polypeptides.

The applied voltage can range from about 1 kV to about 30 kV. Particularly suitable applied voltage can range from about 2 kV to about 25 kV.

Suitable flow rates can range from about 0.5 ml hr$^{-1}$ to about 20 ml hr$^-$. Particularly suitable flow rates can range from about 0.5 ml hr to about 10 ml hr$^{-1}$.

Suitable height of the needle tip to the surface of the collection medium (referred to herein as the "tip to collector distance") can range from about 25 mm to about 300 mm.

Hydrogel microspheres can be stored for later use. The hydrogel microspheres can be stored at about −80° C. to about 22° C. Particularly suitable storage temperatures can be about 4° C. to about 6° C. Hydrogel microspheres can be stored in a slow freeze isopropanol chamber. Another particularly suitable storage temperature can be about −20° C., for example, in a slow freeze isopropanol chamber in −20° C. Another particularly suitable storage temperature can be about −80° C. for example, in a slow freeze isopropanol chamber in −80° C. After freezing, the hydrogel microspheres can be rehydrated. A particularly suitable rehydration method includes incubating the hydrogel microspheres in phosphate buffered saline at 37° C. for about 2 hours.

Hydrogel microspheres can be lyophilized. The hydrogel microspheres can be lyophilized at room temperature for about 1 hour, for example.

Particularly suitable conditions can be, for example, room temperature (RT); low temperatures ranging from about 2° C. to about 4° C.; slow freezing at −80° C.; slow freezing at −80° C. with pre swelling in 10% DMSO; slow freezing at −80° C. with pre swelling in 10% DMSO followed by drying and prolonged storage at −20° C. under argon; slow freezing at −80° C. followed by drying and prolonged storage at −20° C. under argon; drying by lyophilization without pre-storage at −80° C. and prolonged storage −20° C.; and vacuum drying.

Dried hydrogel microspheres can be rehydrated by incubating the hydrogel microspheres in a buffer. Suitable rehydration solutions include, for example, water, phosphate buffered saline, and tris buffered saline. A particularly suitable rehydration method includes incubating the hydrogel microspheres in phosphate buffered saline at 37° C. for about 2 hours.

The rehydration solution used following freezing and drying can further include biological molecules as described herein.

The hydrogel microspheres can be non-degradable or biodegradable (based on the chemical structure of the crosslinkers or the multiarm PEG end moieties). The microspheres are biocompatible and the mild processing conditions make them suitable for encapsulation and delivery of bioactive components like protein and cells or drugs delivery.

In another aspect, the gel precursor solution of the method can further a biological molecule. The biological molecule can be added to the gel precursor solution prior to electrospraying. Suitable biological molecules can be, for example, drugs; cells; proteins; oligopeptides; polypeptides; nucleic acids; and combinations thereof. Suitable drugs can be chemotherapeutics, for example.

Particularly suitable cells include cancer tumor cells. Particularly suitable cancer cells include, for example, glioblastoma cells. Incorporation of cancer cells from cancer tumors advantageously provides a cancer tumor-like structure that more accurately reflects a cancer tumor. It is well known that cancer cells grown in a two-dimensional environment demonstrate a different sensitivity to cancer treatments than do cancer cells grown in a three-dimensional organization. In particular, cancer cells grown as spheroids are more resistant to treatments. Cancer cells grown in three-dimensional liquid suspension cultures also suffer from being limited in size, having an irregular shape, not being amenable to co-culture, and lack tumor matrix interactions of tumors in vivo. Thus, incorporation of cancer cells obtained from cancer tumors into the hydrogel microspheres according to the present disclosure overcomes these drawbacks.

Any protein, oligopeptide, polypeptide, and combinations thereof can be incorporated into the hydrogel microspheres.

Particularly suitable proteins include those in platelet rich plasma. Platelet rich plasma can also be incorporated into the hydrogel microspheres. Particularly suitable proteins include growth factors. Particularly suitable growth factors include, epidermal growth factor (EGF), insulin-derived growth factor (IGF), fibroblast growth factor 2 (FGF2), platelet derived growth factor (PDGF), vascular derived endothelial growth factor (VEGF), transforming growth factor beta (TGF-b), hepatocyte growth factor (HGF), and combinations thereof. Other suitable proteins include serum albumin (e.g., bovine serum albumin), lysozyme, immunoglobulins, and combinations thereof.

In another aspect, the method can further include incubating the hydrogel microspheres in a solution containing the biological molecule. Incubating (or soaking) the hydrogel microspheres in a solution containing a biological molecule "loads" the biological molecule in the hydrogel microparticle. The hydrogel microsphere can be a dried or lyophilized microsphere that is rehydrated in a solution containing a biological molecule. Rehydrating the hydrogel microspheres in a solution containing a biological molecule "loads" the biological molecule in the hydrogel microparticle as the hydrogel microsphere rehydrates.

The disclosure will be more fully understood upon consideration of the following non-limiting Examples.

EXAMPLES

Materials

Four-arm polyethylene glycol tetra-acrylate (10 kDa, 4 arm) (PEG-Ac) was obtained from Laysan Bio. Inc. (Arab, AL). Dithioerthritol (DTT), Olive oil, and all other reagents were obtained from Fisher Scientific unless stated otherwise.
Statistics The results of each experiment were expressed as average±standard deviation. At least 80 particles were counted for each run and a total of 250 to 400 particles were counted for a set of triplicate runs. Polydispersity was calculated as percent coefficient of variance (CV), determined as average of the CV value obtained for each run in a set of triplicate experiments. The groups were compared amongst each other using one way analysis of variance (ANOVA) (Graph Pad Prism). The size distribution graphs were plotted using MATLAB.

Example 1

In this Example, electrospraying was used to prepare polyethyleneglycol hydrogel microspheres.

A 20% w/v stock solution of 4 arm PEG-Ac was made in 0.3 M triethanolamine (TEA) buffer (made in 1× PBS) of pH 7 and pH 7.4. A 5% stock was made for the thiol crosslinkers in 0.3 M TEA buffer of pH 8. To prepare a 10% gel precursor solution the PEG-Ac and thiol crosslinker were combined in 1:2 molar ratio in 0.3 M TEA buffer of either pH 7 or 7.4. Food dye (5% v/v) was also included in the preparation to aid in visualization of the particles. The precursor solution was mixed by gentle pipetting and transferred to a 1 ml syringe. For making the microspheres the syringe was mounted on syringe pump (Harvard Apparatus 22, Biosurplus) to dispense the solution at a desired rate. A high voltage generator (Spellman High Voltage Electronics Corporation) was then used to generate electric field between the nozzle and the collector. The solution was electrosprayed as fine droplets onto a collector having an olive oil bath with a base covered in PARAFILM M® to create a non-stick surface. The gelation of the sprayed droplets was complete within 25 min The formed microspheres were collected by centrifugation and washed 2 times with 0.05% TWEEN 20 in DI water. The electrospraying set-up is depicted in FIG. 1. While using the same general setup as described, the flow rate was varied between 1 ml hr$^{-1}$ to 10 ml hr$^{-1}$, the applied voltage was varied from 0 kV to 25 kV, the nozzle tip to collector distance (TTCD) was varied between 38 mm to 216 mm and the needle gauge was varied between 30 G to 18 G. Experiments were also conducted to determine the effect of final gel concentration on electrospraying PEG particles for which the concentration was varied between 5% w/v to 15% w/v.

Particles were imaged using an inverted microscope (Carl Zeiss). Particle size was analyzed using IMAGE J and the size distribution was determined based on particles count (>300 particles) from three replicate runs.

Example 2

In this Example, gelation time of microspheres formed by electrospraying was investigated to determine the maximum time for electrospraying the particle before completion of gelation.

Figure 2:
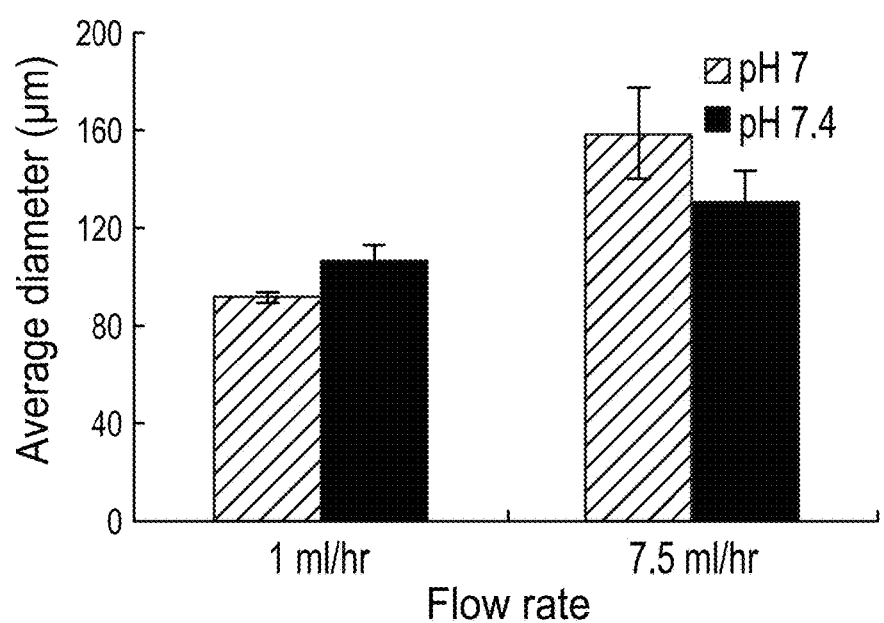
FIG. 2 depicts the effect of buffer pH of PEG hydrogel precursor solution and flow rate on the average microsphere diameter. Runs were carried out at 10 kV applied voltage, flow rates of 1 ml hr$^{-1}$ and 7.5 ml hr$^{-1}$, TTCD of 114 mm, needle gauge of 30 and buffer pH 7 or 7.4. The average diameter is expressed as the mean of three replicate runs with total of 300 microspheres measured. No significant difference between average diameters was observed with respect to pH change, but increased flow rate resulted in larger diameter microspheres.

The hydrogel microspheres formed at three different pHs (7, 7.4 and 8.5) gelled in 23 minutes, 10 minutes, and 1 minute 30 seconds. Thus for the purpose of this study, pH 7 and 7.4 were used for making hydrogel microspheres to provide sufficient time to spray microspheres of the prepolymer solution and then allow them to gel. Furthermore, the microspheres sprayed using precursor solution of pH 7 and 7.4 under identical processing conditions had similar size distribution (FIG. 2).

Example 3

In this Example, collecting medium with different surface properties was investigated to determine adherence of the particles to the collecting medium upon electrospraying.

Collecting media including glass petri dishes, cell culture polystyrene dishes, glass dishes coated with RAIN-X® and PARAFILM M® covered glass base were tested to obtain a hydrophobic, dry and inert surface for collecting microsphere particles.

The PARAFILM M® covered base provided a smooth hydrophobic surface to which the particles being sprayed did not adhere or exhibited minimal adhesion. However, the sprayed particles, being hydrogel, dried up quickly due to water loss by evaporation on the PARAFILM M® covered base.

To prevent hydrogel microsphere drying and obtain well dispersed microsphere particles, the sprayed particles were collected in an oil bath. Three oils tested were olive oil, mineral oil and silicone oil in order of increasing density respectively.

In the case of both olive oil and mineral oil, the electrosprayed droplets sedimented quickly and adhered to the glass collecting base. Silicone oil being very viscous and close in density to water staggered the sedimentation of electrosprayed particles and partially prevented the particles from sticking to the collecting base. However, recovery of the particles from the silicon oil was difficult by simple decantation or centrifugation due to high viscosity of the silicon oil. To further facilitate the collection and obtain a highly hydrophobic surface, an oil bath with the base covered with PARAFILM M® was used for collecting sprayed microspheres. In such a setup the electrosprayed hydrogel particles did not stick to the base covered with PARAFILM M®. Presence of the oil layer over the particle surface also hindered the particle drying by water evaporation from the hydrogel microspheres. Microspheres sprayed under identical conditions either into mineral oil or olive oil had similar sizes. However, particles sprayed into olive oil were easier to collect and separate from the olive oil due to its having a lower viscosity than mineral oil. All further studies were conducted using a glass bowl base covered with PARAFILM M® with a layer of olive oil over it.

Example 4

In this Example, the effect of electrospray mode on generation of droplets was determined.

Figure 3A:
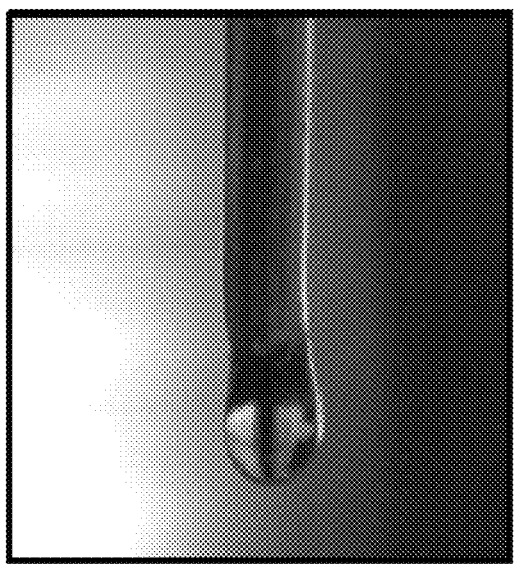
FIGS. 3A & 3B are digital images depicting different modes of droplet formation observed while making PEG microspheres by electrospraying.
Figure 3B:
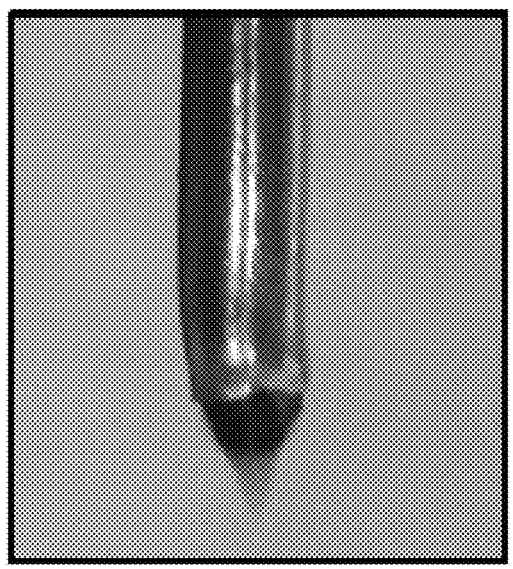

For no applied voltage, large droplets formed that exhibited a diameter of about 2 mm At low flow rates and low voltages dripping was observed. Upon increasing the applied voltage to 10 kV, a transition from dripping to jetting mode resulted in fine droplet formation, thus establishing the critical voltage ($V_{cr}$) for transition to jetting mode (FIG. 3).

The jetting mode was characterized by formation of a stable Taylor cone. The cone jet mode were observed at 10-11 kV at flow rates of 1 ml hr$^{-1}$, 7.5 ml hr$^{-1}$ and 10 ml hr$^{-1}$. At intermittent flow rates, a lot of unstable jet stream was observed. A well-formed Taylor cone was clearly observed at a low flow rate and high voltage. Stability of Taylor cone was also dependent upon the needle gauge. More stable and clear Taylor cones were obtained as the needle gauge was increased from 30 G to 18 G while the applied voltage was 10 kV and a flow rate of 1 ml hr$^{-1}$ was maintained. The applied voltage used to obtain a stable Taylor cone depended on TTCD. A higher applied voltage was required with increased TTCD. Although a stable cone jet mode was observed at certain combinations of operating parameters throughout the run, some sporadic instabilities were observed resulting in solution ejection/spitting, or switch to dripping mode.

Example 5

In this Example, the effect of applied voltage on microsphere size and size distribution was determined PEGAc-DTT microspheres were prepared as described above using a precursor solution having a pH of 7.4. A flow rate of 1 ml hr$^{-1}$, a tip to collector distance of 114 mm and a 30 G needle were used. The applied voltage was varied from 5 kV to 25 kV.

Figure 3C:
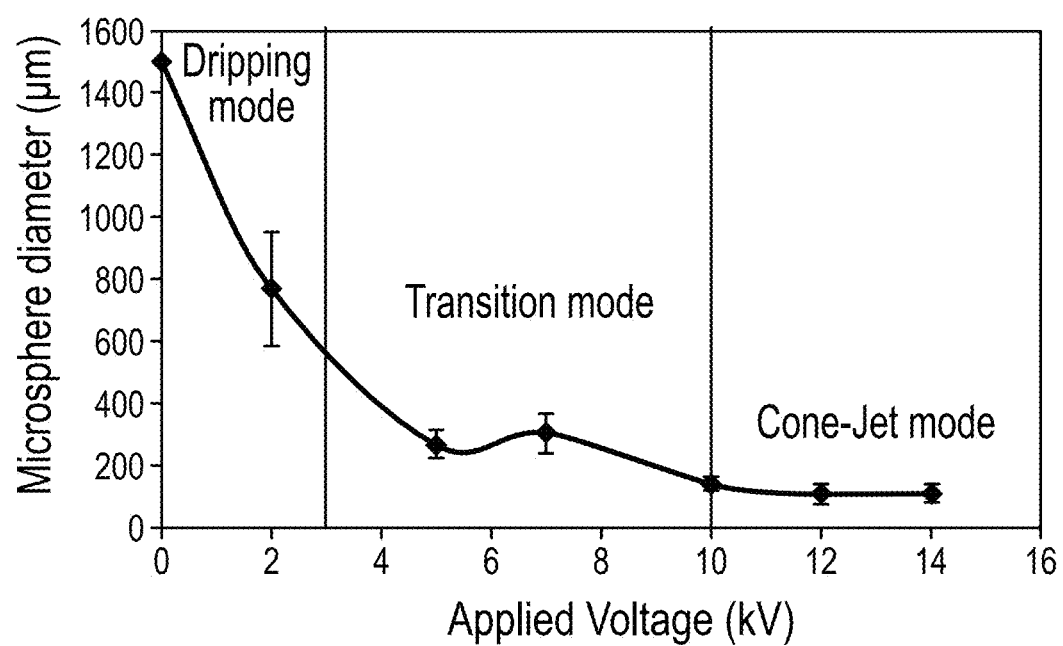
FIG. 3C is a graph depicting the effect of increasing applied voltage on droplet formation and microsphere diameter as the transition from dripping mode to cone jet mode occurred (flow rate=7.5 ml hr$^{-1}$, needle gauge =30 G, TTCD=114 mm, and PEG precursor concentration=10% w/v; p≤0.05). The average diameter is expressed as the mean of three replicate runs with a total of 300 microspheres.
Figure 4A:
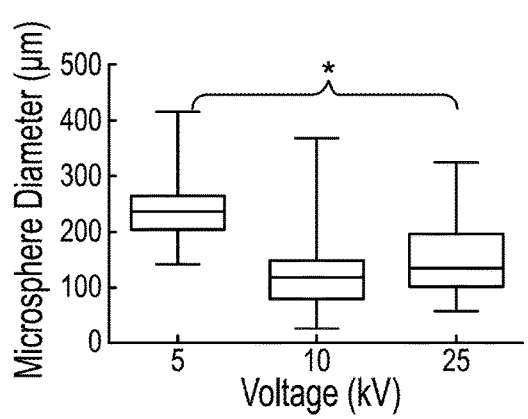
FIGS. 4A-4E depict the effect of applied voltage on PEG microsphere diameter, size distribution, and cell viability.
Figure 4B:
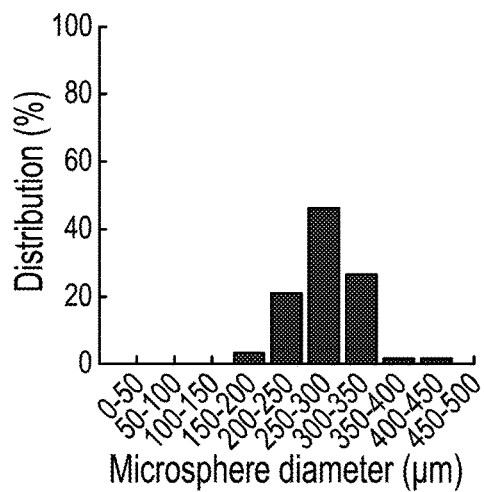
Figure 4C:
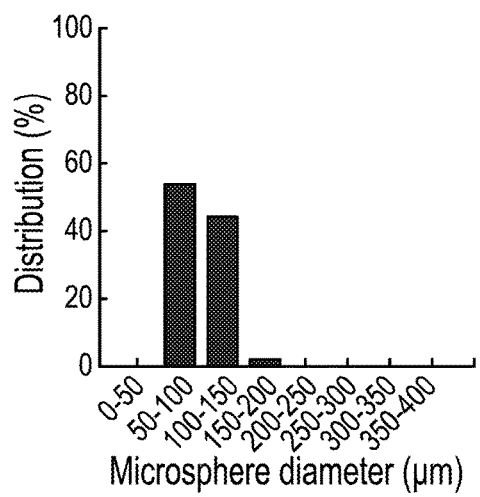
Figure 4D:
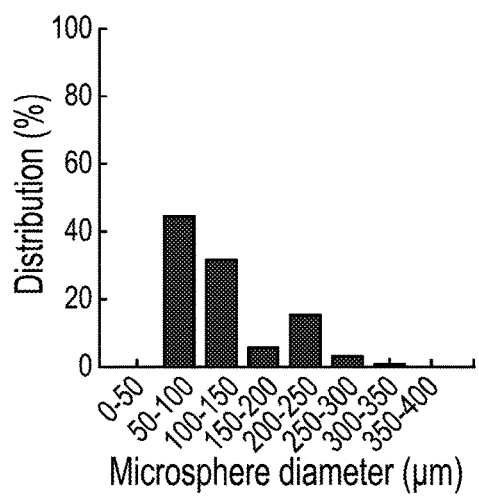
Figure 4E:
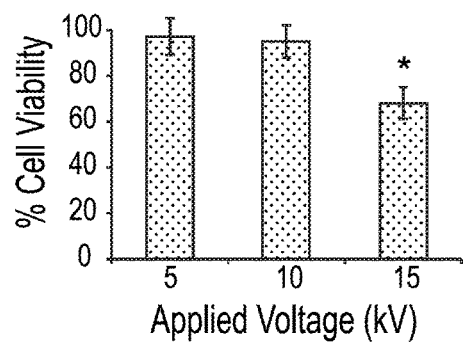

The average particle size changed from 250 to150 µm on applying a positive voltage of 5 kV, 10 kV and 25 kV (FIG. 4A). In general, the particles made at voltages below 10 kV were larger in diameter and had a narrow size distribution (mean diameter at 5 kV was 243 ±38; CV 16%) (FIG. 4A and 4B), while the microspheres made at voltages ≥10 kV were smaller in diameter (50 to 150 µm) with a broader size distribution (CV>30%) (FIGS. 4B & 4C). Applied voltages (while keeping all other parameters constant) above 10 kV did not affect microsphere diameter significantly, thereby reaching the $V_{cr}$ corresponding to jetting mode (FIG. 3C). For instance, microspheres obtained at voltages 10 and 12 kV had similar average diameter of 112±12 µm and 102±19 µm, respectively. Interestingly, there was a small increase in mean microsphere diameter from 112±12 um to 151 ±26 (p≤0.05) when applied voltage was increased from 10 to 25 kV at a constant TTCD. Moreover, compared to 10 kV, microspheres made at 25 kV had wider size distribution (FIGS. 4C and D).

Example 6

In this Example, the effect of flow rate on microsphere size and size distribution was determined PEGAc-DTT microspheres were prepared as described above using a precursor solution having a pH of 7.4. An applied voltage of 10 kV, a tip to collector distance of 114 mm and a 30 G needle were used. The flow rate was varied from 0.005 ml hr$^{-1}$ to 10 ml hr$^{-1}$.

Figure 5A:
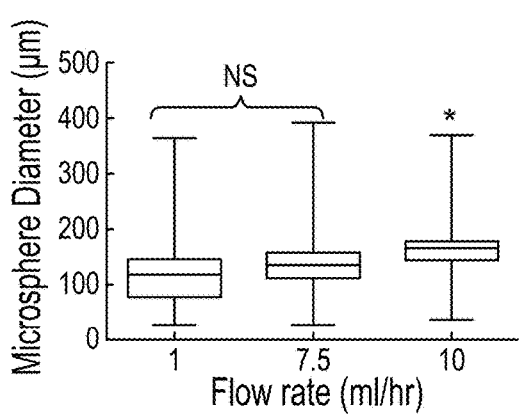
FIGS. 5A-5E depict the effect of flow rate on PEG microsphere diameter, size distribution, and cell viability.
Figure 5B:
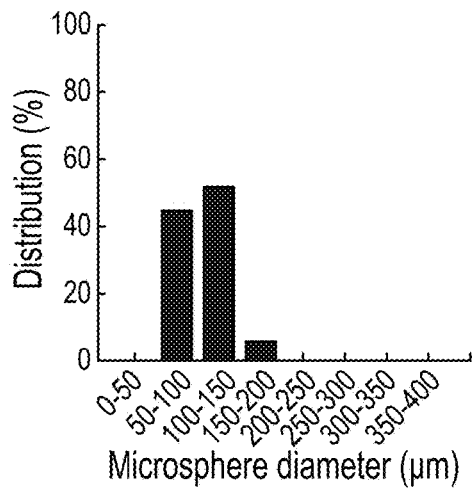
Figure 5C:
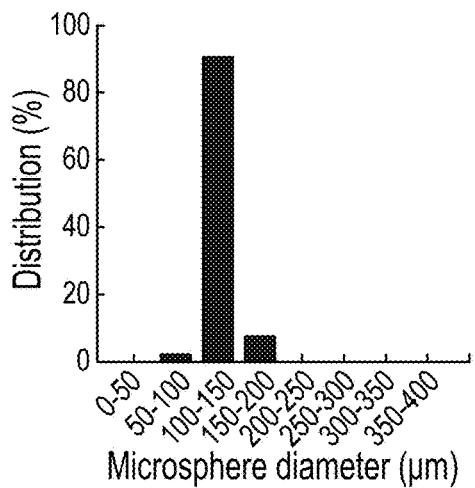
Figure 5D:
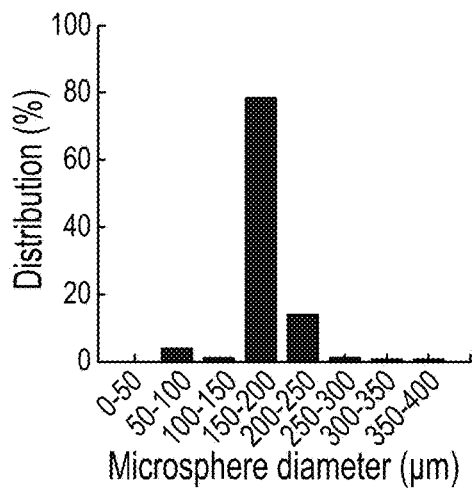
Figure 5E:
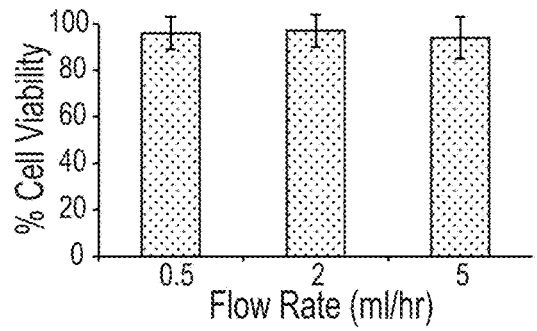

At very low flow rates of <0.5 ml hr$^{-1}$ PEG solutions of pH 7.4 gelled before the complete solution could be sprayed. Thus, all solutions were sprayed at a rate 1 ml hr$^{-1}$. At all flow rates tested, the $V_{cr}$ to obtain a stable Taylor cone was found to be 10 kV at constant TTCD of 114 mm and 30 G needle. At very high flow rates ≥10 ml hr$^{-1}$ sporadic instabilities in jetting mode were observed. Thus, all further experiments were conducted in the range of 1-10 ml hr$^{-1}$. Overall, a minimal increase in microsphere diameter was observed with increase in flow rate (FIG. 5A). For flow rates of 1 ml hr$^{-1}$ and 7.5 ml hr$^{-1}$, the mean microsphere diameters of 119±19 µm (CV 32%) and 130±13 µm (CV 32%), respectively, were not significantly different, they were was significantly different from mean diameters of microspheres obtained at a 10 ml hr$^{-1}$ flow rate (187±62 µm, CV 23%, p≤0.05) (FIG. 5A). Although the mean microsphere diameter obtained at flow rates of 1 ml hr$^{-1}$ and 7.5 ml hr$^{-1}$ were not significantly different, the microsphere size distribution differed (FIGS. 5B & C). As the flow rate was increased, the percentage of microspheres in the diameter range of 100 µm to 150 µm increased from 29.5% for 1 ml hr$^{-1}$ to 59.7% for 7.5 ml hr$^{-1}$. Similarly, microspheres obtained at 10 ml hr$^{-1}$ had only 14.7% of microspheres below 100 µm as opposed to 56.0% at 1 ml hr$^{-1}$ and 31.0% at 7.5 ml hr$^{-1}$ (FIG. 5).

Example 7

Figure 6A:
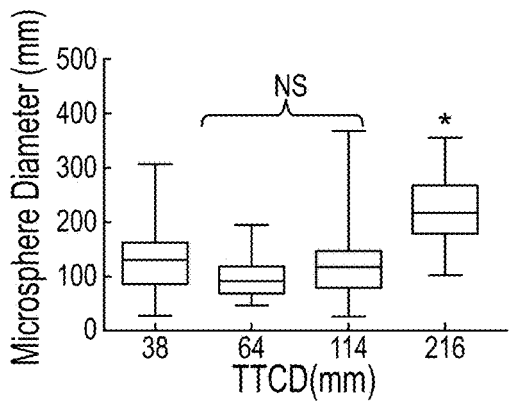
FIGS. 6A-6E depict the effect of TTCD on PEG microsphere size and size distribution.
Figure 6B:
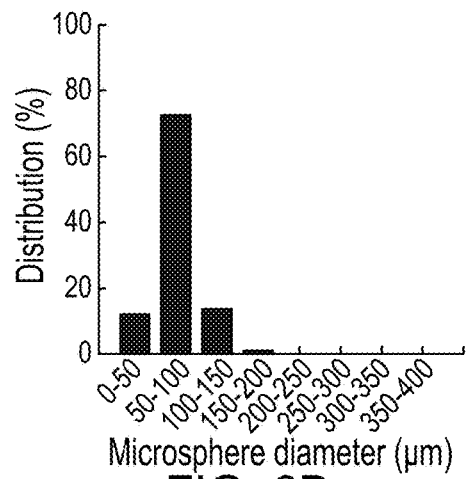
Figure 6C:
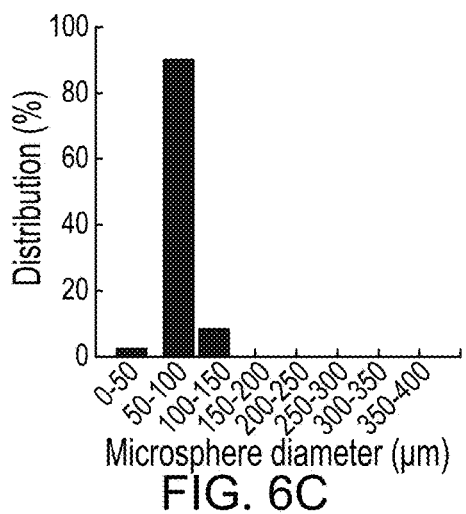
Figure 6D:
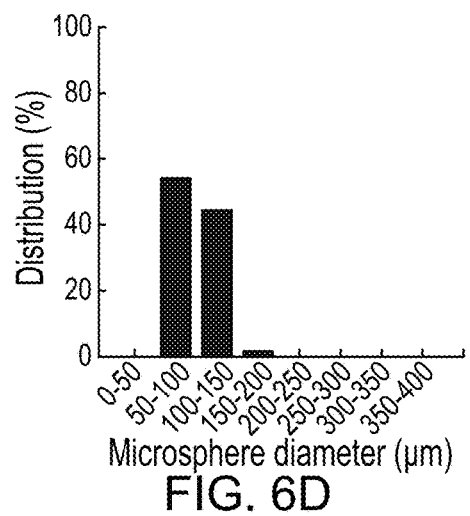
Figure 6E:
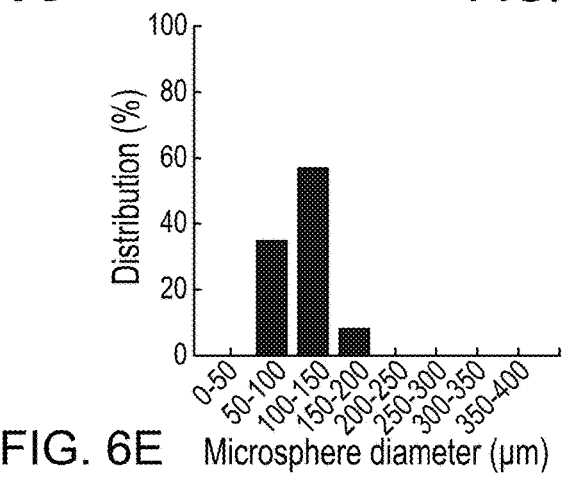

In this Example, the effect of tip to collector distance (TTCD) on microsphere size and size distribution was determined PEGAc-DTT microspheres were prepared as described above using a precursor solution having a pH of 7.4. An applied voltage of 10 kV, a flow rate of 1 ml hr$^{-1}$ and a 30 G needle were used. The tip to collector distance was varied from 38 mm to 216 mm For a constant applied voltage of 10 kV and flow rate of 1 ml hr$^{-1}$ the microsphere size was not influenced by the TTCD up to 114 mm (FIG. 6). The mean microsphere diameter of the microspheres sprayed at a TTCD of 38, 64 and 114 mm was 129±49 µm (CV 27%), 97±21 µm (CV 26%), and 119±19 µm (CV 32%), respectively and was not significantly different (p>0.05). However, above a TTCD of 114 mm the mean microsphere diameter increased as the TTCD was increased while keeping other parameters constant. Under constant voltage conditions we found that there was an optimum for TTCD: too low or too high TTCD resulted in either wider diameter distribution or increase in microsphere diameter. For TTCD distance greater than 203 mm and 10 kV applied voltage, an increase in mean diameter was observed (FIG. 6A and E). However, when the microspheres were sprayed at a TTCD of 200-216 mm with a corresponding increase in applied voltage from 10 kV to 15 kV, microspheres of diameters 50 - 100 pm were obtained (Table 1, Condition 7). Similarly, the $V_{cr}$ for a TTCD of 64 mm was found to be 8 kV and resulted in microsphere diameters equivalent to others sprayed at 114 mm and 10 kV (Table 2, Condition 4).

TABLE 2

Fabrication parameters for applied voltage, TTCD and needle gauge. Rows shaded in gray indicate critical voltage at a given TTCD and needle gauge.

| Condition | Mean Diameter (µm) | Voltage (kV) | Height (mm) | Needle Gauge (G) | % CV (mean of 3 runs) |
|---|---|---|---|---|---|
| 1 | 772 ± 184 | 2 | 114 | 30 G | 12 |
| 2 | 533 ± 139 | 8 | 64 | 18 G | 26 |
| 3 | 243 ± 33 | 5 | 114 | 30 G | 16 |
| 4 | 123 ± 10 | 8 | 64 | 30 G | 26 |
| 5 | 119 ± 19 | 10 | 114 | 30 G | 32 |
| 6 | 72 ± 3 | 10 | 114 | 18 G | 38 |
| 7 | 64 ± 18 | 15 | 216 | 30 G | 28 |
| 8 | 80 ± 11 | 15 | 216 | 18 G | 13 |

Example 8

In this Example, the effect of needle gauge on microsphere size and size distribution was determined.

PEGAc-DTT microspheres were prepared as described above using a precursor solution having a pH of 7.4. An applied voltage of 10 kV, a flow rate of 1 ml hr$^{-1}$ and a tip to collector distance of 114 mm were used. The needle gauge was varied from 30 G to 18 G.

Figure 7A:
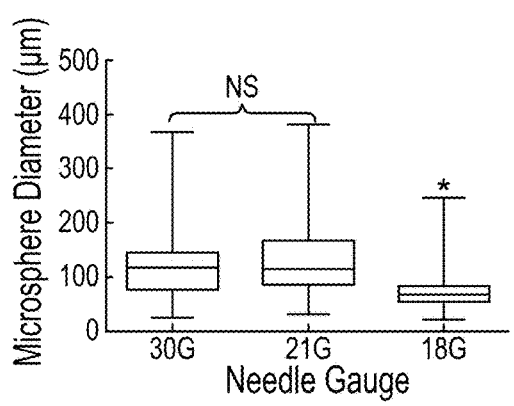
FIGS. 7A-7E depict the effect of needle gauge on PEG microsphere size, size distribution, and cell viability.
Figure 7B:
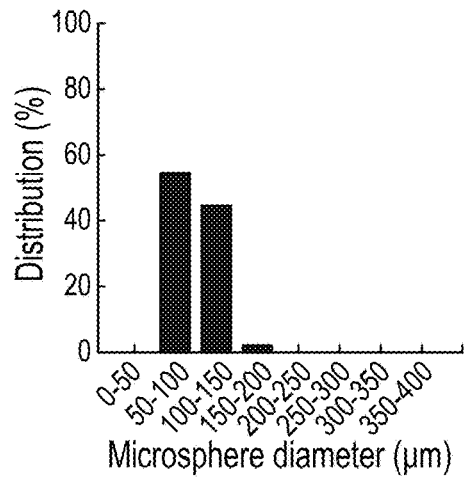
Figure 7C:
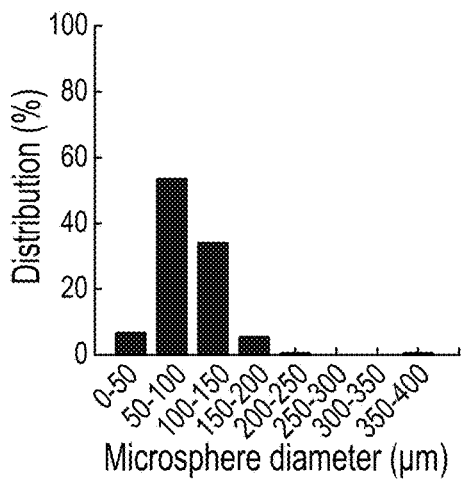
Figure 7D:
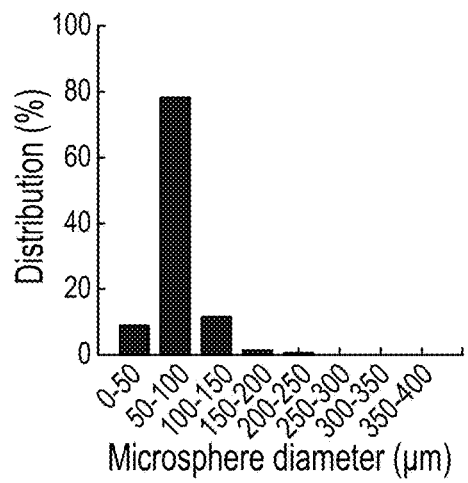
Figure 7E:
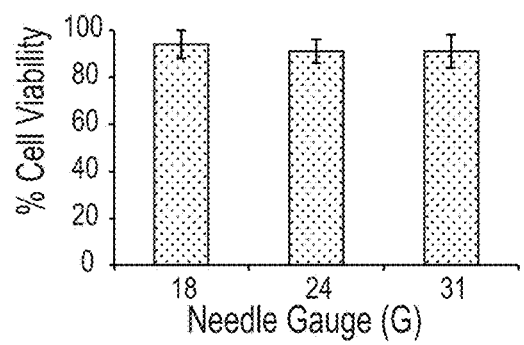

For an applied voltage of less than 10 kV and TTCD less than 114 mm, the needle gauge had a strong influence on microsphere diameter (Table 1). For example, microspheres made at 8 kV and 64 mm TTCD using 30 G and 18 G needles had mean diameters of 123±10 µm (CV 26%) and 533 ±139 µm (CV 26%), respectively (p≤0.05). Moreover, a Taylor cone formation was observed for 30 G needle while dripping was seen when 18 G was used under the same parameters, indicating influence of needle gauge on $V_{cr}$. This influence was negligible at applied voltages beyond 114 mm TTCD and 10 kV voltage (FIG. 7). Although a Taylor cone formation was observed beyond TTCD of 114 mm and 10 kV, the mean microsphere diameter was found to depend upon the needle gauge. The mean microsphere diameter for electrospraying using needle gauges 30 and 21 at TTCD of 114 mm and voltage of 10 kV (119±19 µm (CV 32%) and 125±34 µm (CV 40%), respectively) was similar but significantly larger than mean microsphere diameter obtained by using an 18 G needle (72±28 µm, CV 38%) (FIG. 7A). This could be due to a formation of a more stable cone with a decrease in needle gauge. With further increment increases in both voltage and TTCD, the effect of needle gauge on mean microsphere diameter became minimal. For example, the mean microsphere diameter of microspheres electrosprayed using an 18 G needle at 10 kV was similar to the microsphere diameter obtained when PEG hydrogel microspheres were electrosprayed at 15 kV, 216 mm TTCD and 1 ml hr$^{-1}$ using either 30 G or 18 G needles (Table 2).

Example 9

In this Example, the effect of the concentration of PEGAc-DTT prepolymer solution on microsphere size and size distribution was determined PEGAc-DTT microspheres were prepared as described above using a precursor solution having a concentration from 5% w/v to 15% w/v. The prepolymer solution had a pH of 7.4. An applied voltage of 10 kV, a flow rate of 1 ml hr$^{-1}$, a tip to collector distance of 114 m, and needle gauge of 30 G were used.

Figure 8:
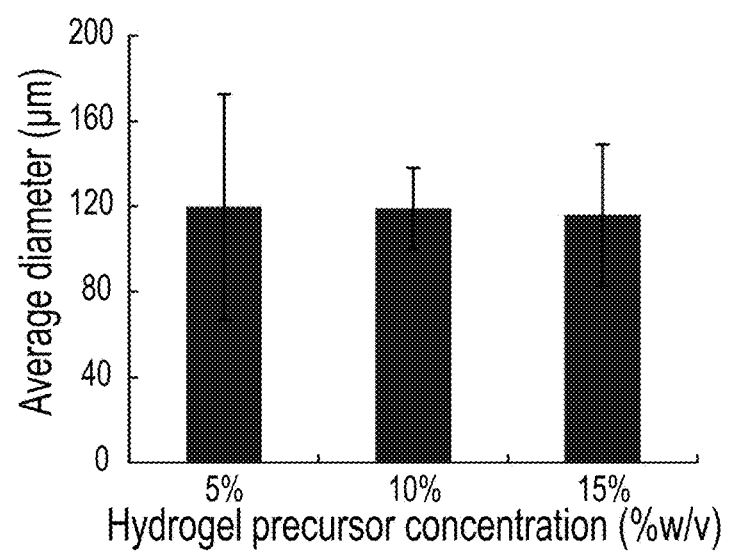
FIG. 8 depicts the effect of hydrogel precursor concentration on PEG microsphere diameter. All runs were carried out at 10 kV applied voltage, flow rate of 1 ml hr$^{-1}$, TTCD of 114 mm, needle gauge of 30 and buffer pH 7.4. The average diameter is expressed as the mean of three replicate runs with total of 300 microspheres measured. No significant difference between average diameters was observed.

PEG solutions having concentration of 5% w/v, 10% w/v, 15% w/v were electrosprayed had similar particle size distributions and no significant difference was found (FIG. 8).

Example 10

In this Example, hydrogel microspheres were evaluated for storage under different conditions.

PEG microspheres were prepared as described above and kept at 4-6° C., −20° C., −80° C. conditions. The microspheres were lyophilized to ensure particle stability upon storage. Microspheres stored at 4° C. were imaged and weighed at 7 day intervals over a 28 day period. Diameters were documented to observe swelling/degradation of microspheres during this time. For microspheres stored in −20° C. and −80° C. conditions, microspheres were stored in a slow freeze isopropanol chamber in −20° C. or −80° C. for 24 hours. Microspheres were then removed, imaged, and placed in 1 mL of PBS in a 37° C. oven for 24 hours for rehydration after the freezing process. Microspheres were lyophilized and then rehydrated for 24 hours in 1 mL of PBS at 37° C. Images were analyzed to evaluate structural deformations induced from each storage condition. Changes in swelling were based on change in diameter measurements and swollen weight change. Degradation was assessed by visual observations.

Figure 9A:
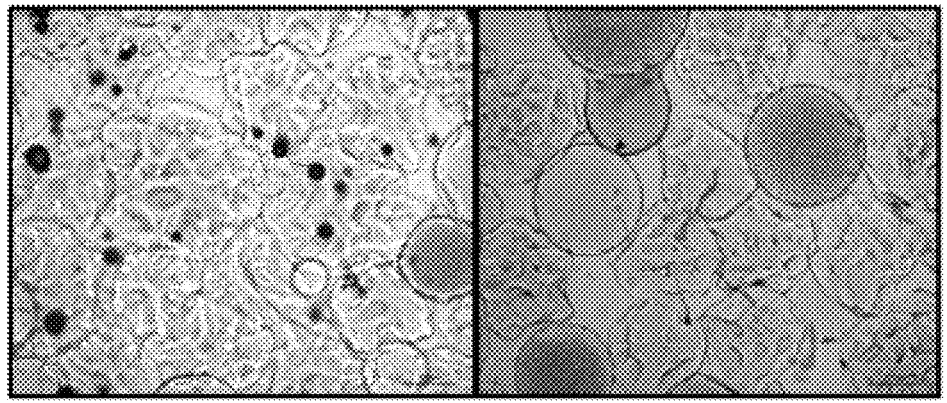
FIGS. 9A-9C are photomicrograph images depicting the storage of PEGAc-DTT hydrogel microspheres at different temperatures and evaluation of their re-swelling characteristics.
Figure 9B:
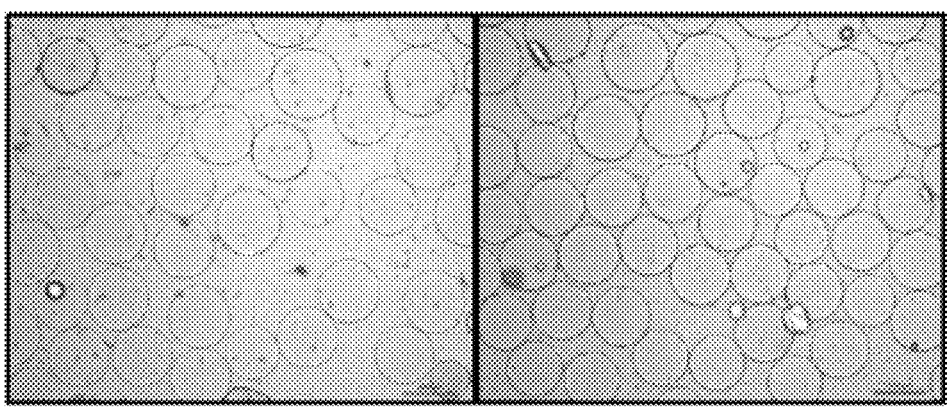
Figure 9C:
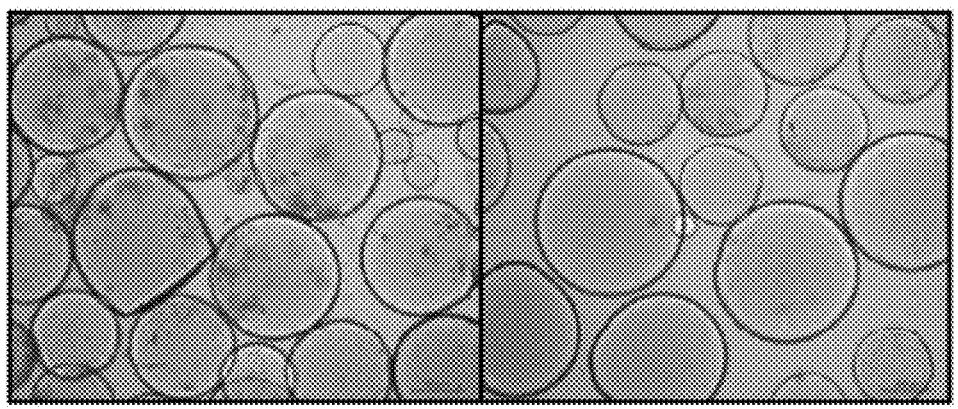
Figure 10:
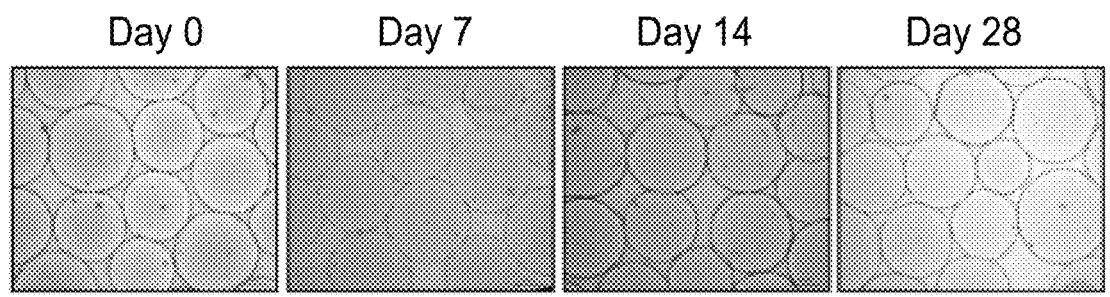
FIG. 10 are photomicrographs depicting PEGAc-DTT hydrogel microspheres stored at 4° C. for Day 0 (just after fabrication), Day 7, Day 14 and Day 28.

Polyethylene glycol hydrogel microspheres were found to be resilient to different storage regimes. PEG microspheres stored at −20° C. by slow controlled freezing or lyophilized regained their original shape upon rehydration (FIG. 9A). Contrastingly, when the particles were stored at −80° C. by slow controlled freezing, rehydration of the particles did not restore the original smooth spherical geometry even after 24 hours (FIG. 9B). The freezing rate also seemed to have influenced the retrieval and maintenance of spherical morphology of the hydrogel microspheres. When the hydrogels were flash frozen either at −80° C. or −20° C., the hydrogels lost their smooth spherical surface and did not recover after rehydration. Evaluation of physical properties particles was also done after the microspheres were kept at 4° C. The results indicated that immediately after synthesis, particles can be stored for long storage times in their native state at 4° C. The particles did not show any significant signs of degradation as evident by negligible change in size. FIG. 10 depicts representative images of the microspheres at different time points up to 28 days. The images demonstrate that the particles maintain their physical shape and characteristics throughout the period of study.

Example 11

In this Example, the incorporation of cells into hydrogel microspheres was investigated.

Hydrogel microspheres were prepared by coupling sulfhydryl terminated adhesive ligands (RGD) to 4-arm PEG-Ac. The SH terminated 4-arm PEG-Ac was then mixed with PEG-diester-dithiol crosslinker and cell suspensions. For analysis of cell type, the cells used were U87 glioblastoma cells, primary fibroblasts, and INS-1 glioblastoma cells. For analysis of cell density, $10^6$ cells/milliliter, $10^8$ cells/milliliter and $10^9$ cells/milliliter were incorporated into hydrogel microspheres. Microspheres were prepared as described above, collected in an olive oil collection medium, washed in 1× PBS and allowed to polymerize resulting in encapsulation of the cells.

Figure 11A:
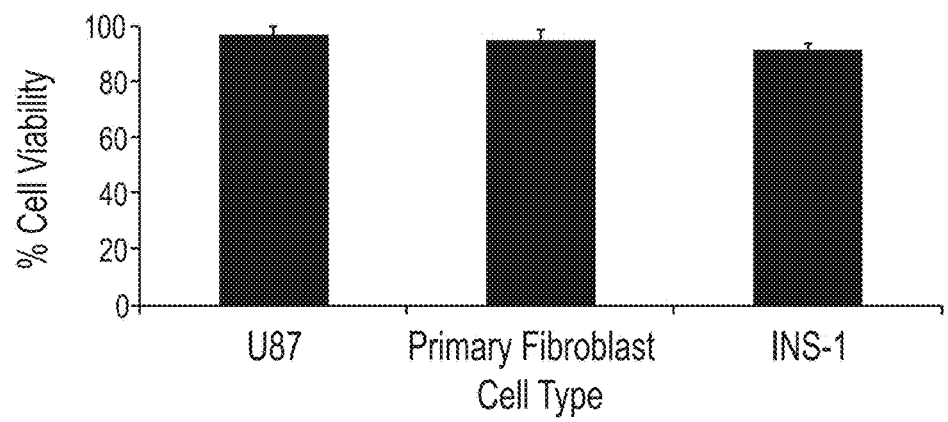
FIG. 11A is a graph depicting the effect of cell type on cell viability post encapsulation in PEG microspheres.
Figure 11B:
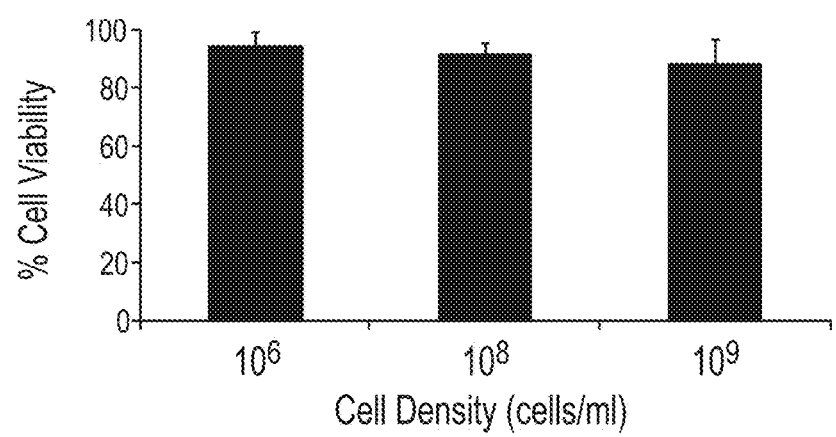
FIG. 11B is a graph depicting the effect of cell density on cell viability post encapsulation in PEG microspheres.

As shown in FIG. 11A, different cell types remained viable when incorporated into hydrogel microspheres. As shown in FIG. 11B, cell density within hydrogel microspheres did not affect cell viability.

Example 12

In this Example, the release of proteins incorporated into hydrogel microspheres was investigated.

A hydrogel precursor solution was prepared using 6-Arm PEG-Ac and DTT made at 10% w/v concentration and 1:1 molar ratio of acrylate to thiol in 0.3M TEA (pH 7.0). were separately added followed by polymerization of microspheres to form hydrogel microspheres with protein incorporated within the hydrogel microspheres. Proteins (2% w/v Lysozyme, bovine serum albumin (BSA), platelet rich plasma, immunoglobulin (IgG), and thrombin and platelet rich plasma "PRP") were encapsulated during hydrogel microsphere fabrication as described. Protein release was measured by Bradford assay at different time intervals to determine effective diffusion.

Figure 12:
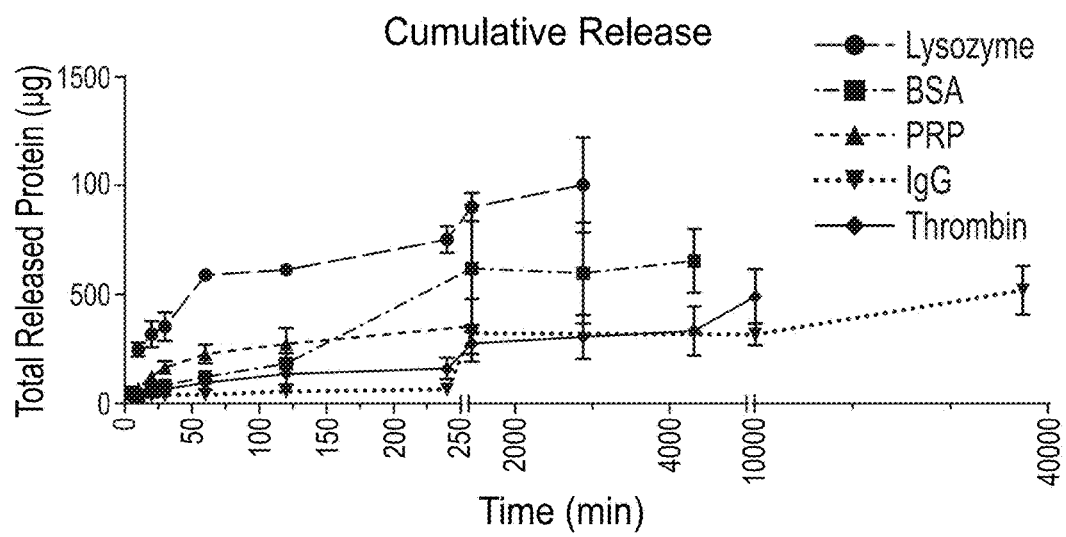
FIG. 12 are graphs depicting the release of lysozyme, bovine serum albumin (BSA), platelet rich plasma, immunoglobulin (IgG), and thrombin from hydrogel microspheres over time.
Figure 13:
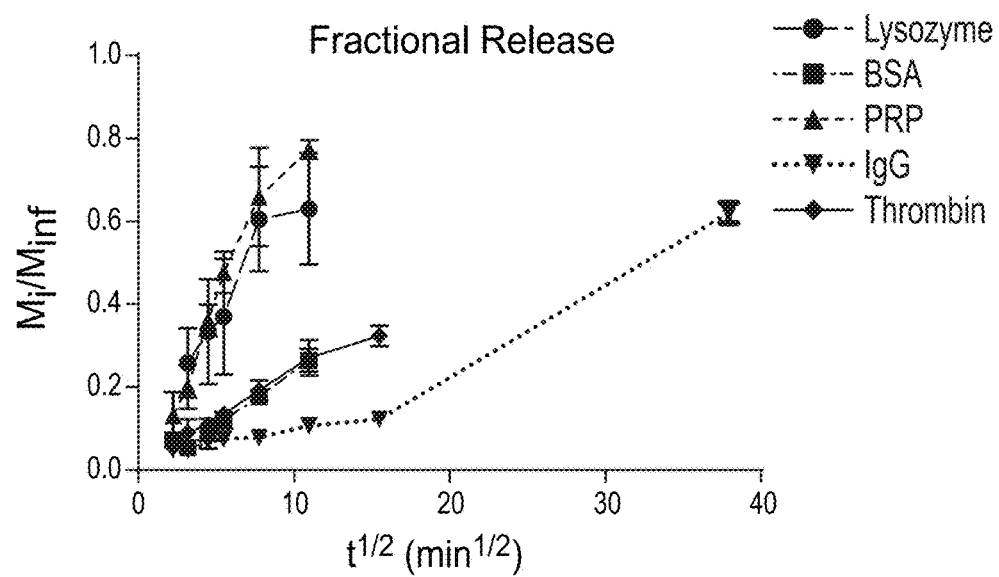
FIG. 13 depicts the fractional release of lysozyme, bovine serum albumin (BSA), platelet rich plasma, immunoglobulin (IgG), and thrombin from hydrogel microspheres.

As shown in FIGS. 12 and 13, medium molecular weight proteins such as BSA and thrombin had faster diffusion rates than heavier proteins such as IgG. Diffusion rate could be controlled by molecular weight and hydrodynamic radii of protein, and mesh size and degradation rate of hydrogel.

Example 13

In this Example, the effect of storage conditions on equilibrium swelling of hydrogel microspheres was evaluated.

PEG hydrogel microspheres were prepared by electrospraying. Freshly prepared stock solutions of 4 arm PEGAc (20% w/v) and DTT (5% w/v) in 0.3 M triethanolamine (TEA) in 1× phosphate buffered saline (PBS) pH 7.4 were used to prepare a 10% gel precursor solution. The stock solutions were combined in 1:1 molar ratio of acrylate to thiol in 0.3 M TEA buffer pH 7.4. For aiding visualization of microspheres 5% v/v blue food dye was also included in the preparation. The precursor solution was mixed and transferred to a 1 ml syringe having a blunt 18 G needle attached at one end. The syringe was mounted on a syringe pump (Harvard Apparatus 22, Biosurplus). A high voltage power supply (Spellman High Voltage Electronics Corporation) was then used to generate an electric field of between the needle tip and the collector a Teflon coated pan. For making microspheres, the solution was electrosprayed at flow rate of 2 ml h$^{-1}$, an applied voltage of 15 kV and tip to collector distance of 216 mm The sprayed microspheres were collected in a Teflon coated pan filled with 50 ml of olive oil. The gelation of the sprayed droplets was complete within 25 minutes. The microspheres were collected by centrifugation and washed twice with PBS. Hydrogel microspheres post-washed with PBS were allowed to swell for 1 hour to reach equilibrium swelling and were weighed after blotting with KIMWIPE® to obtain the swollen weight. The hydrogel microspheres were then centrifuged to remove excess PBS, blotted with a KIMWIPE® to remove excess PBS and subjected to one of the specified conditions of storage for 7 and 30 days respectively. 1) room temperature (RT); 2) 4° C. (Fridge); 3) slow freezing at −80° C.; 4) Slow freezing at −80° C. with pre swelling in 10% DMSO for 2 hours; 5) Slow freezing at −80° C. with pre swelling in 10% DMSO for 2 hours followed by lyophillization and prolonged storage −20° C. under argon; 6) Slow freezing at −80° C. for 2 hours followed by lyophillization and prolonged storage −20° C. under argon; 7) Lyophillization without pre-storage at −80 ° C. and prolonged storage −20° C.; and 8) Vacuum drying All conditions of storage tested included keeping swollen microspheres at RT, slow freezing and extended storage at negative 80 (−80° C.), −80° C+DMSO and refrigerated (4° C.). While three test conditions involved storing beads under dry conditions which all involved lyophillization of microspheres after storage at −80° C. with and without pre swelling in DMSO containing PBS or vacuum drying using lyophillization without pre-storage under freezing conditions. Each run of the electrosprayed hydrogel microspheres was divided into two equal parts. One half was stored at one of the indicated conditions and the other half was used as RT control to obtain the pre-storage swelling ratio of the same. The swollen weight of the pre-storage control and post-storage microspheres was obtained by swelling the microspheres for 2 hours in PBS, centrifuged and blotted dry with KIMWIPE®, weighed to obtain the swollen weight ($M_S$). The microspheres were then dried at 60° C. for 24 hours to ensure complete drying and weighed to obtain the dry weight ($M_D$). The equilibrium swelling ratio was then calculated as $Q_M=M_S/M_D$. The % change in swelling ratio was calculated by divining $Q_M$ of post-storage microspheres/$Q_M$ of pre-storage control microspheres) ×100.

To evaluate changes in mechanical properties as result of different storage conditions, storage and loss modulus G' and G" of hydrogels was measured pre and post-storage. All rheology experiments were conducted using an AR-2000 ex rheometer (TA Instruments) and 20 mm parallel plate geometry. The absence of slip was verified by running experiments with various gap heights. A frequency of 1-10 rad/s and constant strain of 1% was used for testing of all hydrogels, which was within the linear viscoelastic region (LVR). A 10% w/v PEG hydrogels (as previously described) were made as 20 mm diameter disc of 0.5 mm thickness and swelled in lx PBS, pH 7.4. The hydrogels were blotted carefully prior to measurements at the swelling equilibrium. The hydrogels were then stored for 7 days at the specified conditions and then re-swelled for 24 h in PBS and evaluated for G'.

The change in shape and microstructure of the microspheres post storage was evaluated by environmental scanning electron microscope (ESEM) at swelling equilibrium. The ESEM images of the swollen microspheres taken post storage were compared to pre-storage RT controls.

For microsphere degradation analysis, hydrogel microspheres were stored for either 7 or 30 days at specified conditions and then swollen to equilibrium in 1XPBS. The hydrogel microsphere were then stored in 1XPBS at RT. The hydrogel microspheres were imaged at regular time intervals. The hydrogel microspheres diameter was measured as specified. The percent change in number of diameter in different size range was estimated to evaluate the degradation of the microspheres.

For protein diffusion analysis, the diffusion of bovine serum albumin (BSA) in the hydrogels in control hydrogels and hydrogels stored for 7 days was measured using FCS as per the procedure described elsewhere. The hydrogels were cut with a 6 mm biopsy punch to ensure the gels would fit in the chambers post-swelling. For FCS studies, hydrogels were placed in a chambered cover glass (Nalgen Nunc International, Rochester, N.Y.). The hydrogels were soaked in a 150 nM solution of BSA in 1× PBS for at least 24 hours prior to FCS measurement. The chambers were covered with aluminum foil and placed in a dark area to avoid unwanted light interaction. The BSA was labeled with Atto 532

NHS-ester dye ((Sigma Aldrich, St. Louis, Mo.) as per the manufacture protocol at a molar excess of 7. Unbound fluorophores were removed using Fluorescent Dye Removal Columns (Thermo Scientific, St. Louis, Mo.) as per the manufacture protocol with a degree of labeling of 5.02. The average diffusion time ($\tau_D$) was calculated for each hydrogel. The effective diffusivity of each solute in water (D0) was calculated by the Stokes-Einstein equation.

For statistical analysis of each run and storage condition, at least 80 to 100 microspheres were counted and a total of 250 to 400 microspheres were counted for a set of triplicate runs or storage condition. The results of each experiment were expressed as average ±standard deviation. Polydispersity was calculated as percent coefficient of variance (CV) determined as average of the CV value obtained for each run in set of triplicate experiments. The groups were compared amongst each other using one way analysis of variance (ANOVA). Individual set of groups were compared using student T test in Microsoft excel. The size distribution graphs were plotted using MatLab.

Figure 14:
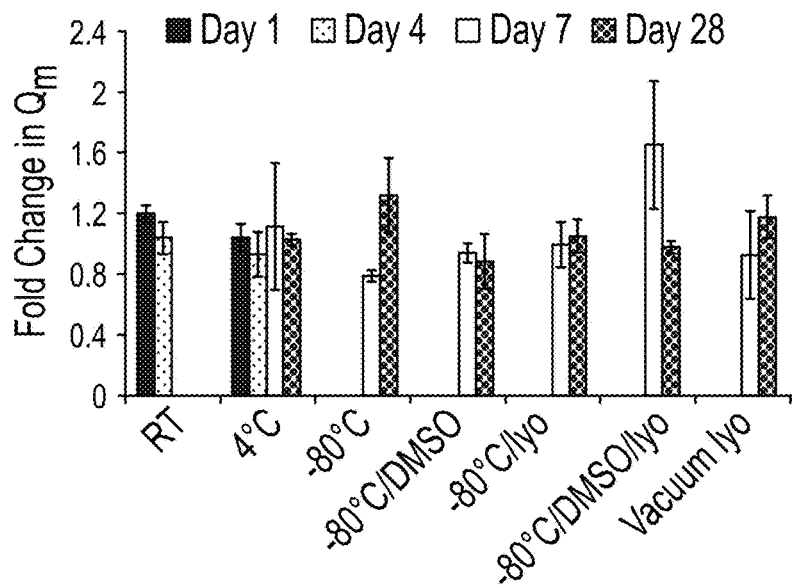
FIG. 14 is a graph depicting the fold change in swelling ratio post storage at different conditions for different lengths of time.

None of the microspheres stored at the above mentioned storage conditions showed a statistically significant fold change in the equilibrium swelling ratio in comparison to the control microspheres post storage (FIG. 14). Our results indicate that degradable microspheres could be stored under the common conditions of storage conditions for 7 to 30 days without change in their swelling ratio. It was rather unexpected for long storage times at 4° C. since the microsphere were stored under moist conditions without compete removal of PBS which could have led to significant amount of degradation in the microspheres formed of biodegradable crosslinks between PEG Ac and thiol. The microspheres stored at −80° C. by slow freezing for 30 days showed a slight increase in swelling ratio while microspheres stored by pre-swelling in 10% DMSO showed a slight decrease in the swelling ratio. However, compared to other swelling ratio of microspheres stored under other conditions this was non-significant. This small increase in swelling ratio could arise due to experimental error. Further as expected the microspheres kept at RT had 1.5× fold change in the swelling ratio post-storage for 30 have. This was rather a very slow change considering that the microspheres have ester linkages which are very susceptible to hydrolytic degradation.

Figure 15:
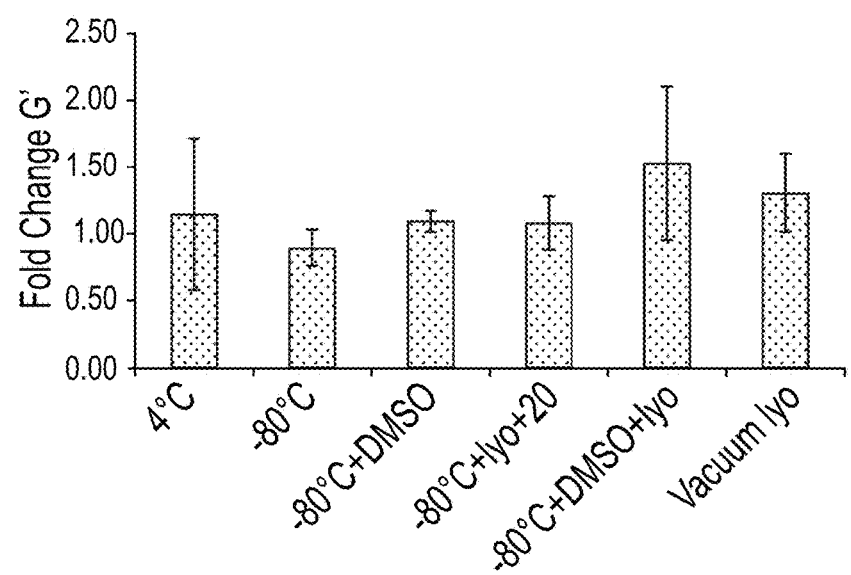
FIG. 15 is a graph depicting the fold change in storage modulus post storage at the indicated conditions for day 7.

Due to complexity involved in measuring the mechanical strength of the hydrogel microspheres and low modulus which made it difficult to measure the change in their modulus post storage consistently and reproducibly, the mechanical strength of hydrogel discs of 20 mm in diameter was measured. The hydrogels stored by slow freezing at −80° C. showed a slight decrease in the mechanical strength compared to RT controls while hydrogel stored by slow freezing at −80° C. by pre swelling in 10% DMSO followed by lyophilization and vacuum drying using lyophilization without pre-storage at −80° C. showed a slight increase in the modulus (FIG. 15). Comparing the hydrogel stored at different conditions to their respective RT controls and amongst each other did not show statistically significant differences.

Figure 16A:
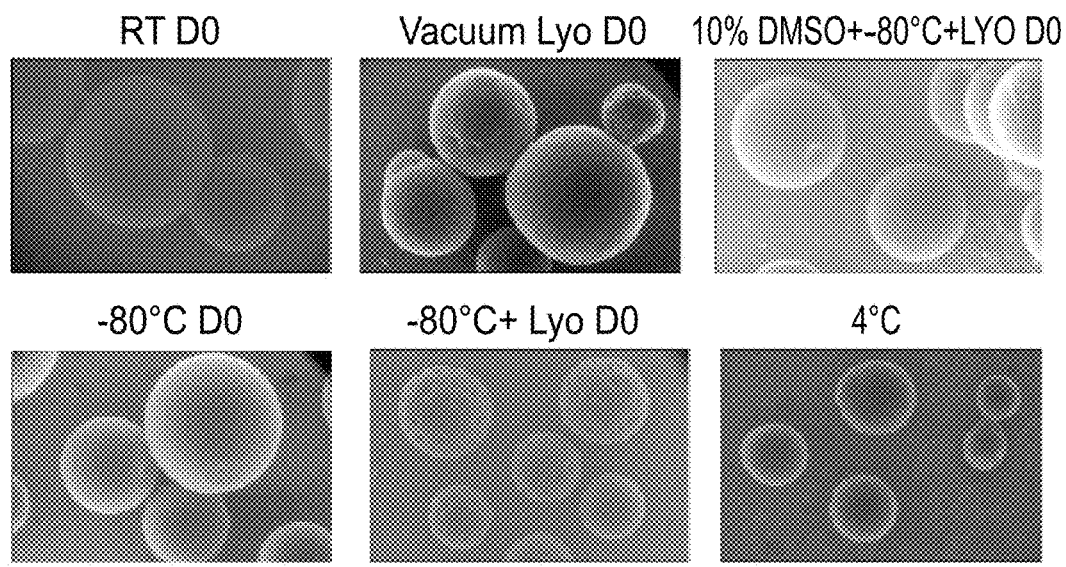
FIG. 16A are environmental scanning microscope images of hydrogel microspheres post storage day zero just after storage (day 0).
Figure 16B:
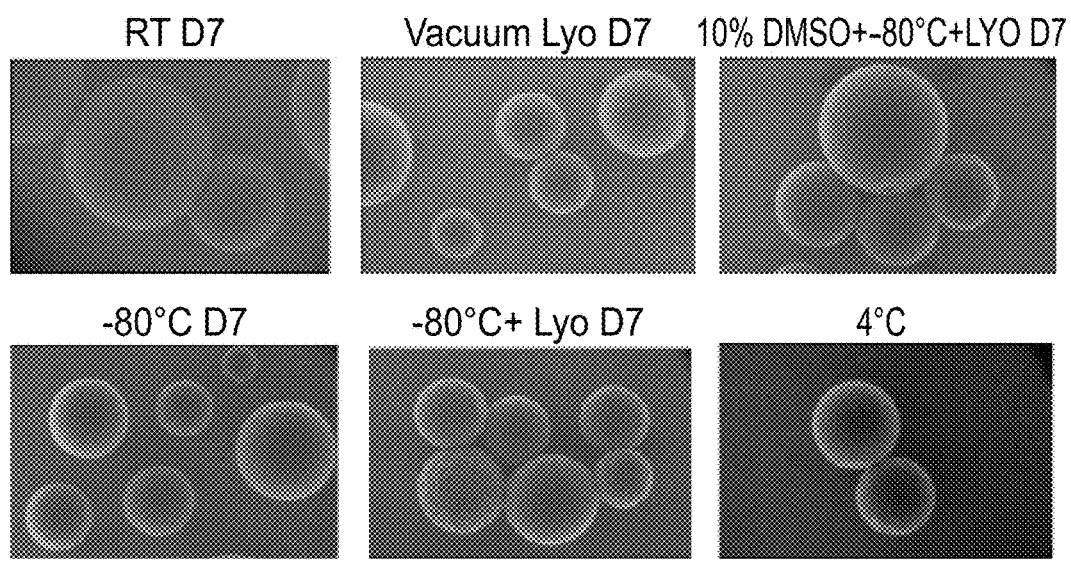
FIG. 16B are environmental scanning microscope images of hydrogel microspheres post storage at day 7 after storage.

The diameter of hydrogel microspheres was measured post storage at specified conditions for 7 and 30 days. FIGS. 16A & 16B show digital images of swollen hydrogel microspheres after storage at different conditions. Images show that upon re-swelling post storage at specified conditions, the hydrogel microspheres swell back to their original size and shape. Hydrogel microspheres that were lyophilized before storage at −20° C. for 7 days or 30 days had distinct rough and irregular surfaces contrary to the smooth and spherical surface observed in hydrogel microspheres either not stored under different conditions or stored at RT.

ESEM analysis was used to study hydrogel microspheres stored under different conditions (FIG. 17) Storage of microspheres under specified conditions for different period of time day 0, 7 and 30 days did not affect their surface morphology upon re-swelling in PBS. Hydrogel microspheres that were lyophilized prior to storage had surface pores that depended upon the pre-processing condition used for the hydrogel microspheres. The hydrogel microspheres either slow freeze at −80° C. prior to lyophilization or directly lyophilized showed surface pores. Slow freezing at −80° C. by pre-swelling in 10% DMSO followed by lyophilization prevented formation of the surface pores in the hydrogel microspheres. Further analysis of the microspheres on day 0 post processing for the specified storage conditions showed similar trends on day 7 and day 30. This indicated that the processing conditions used for storage directly affected the hydrogel microspheres. Surface pores were not observed in hydrogel microspheres stored at −80 C with or without pre swelling equilibration in 10% DMSO (FIGS. 16A & 16B).

The microsphere degradation rate post storage under different conditions was analyzed and compared to their degradation rate at 37° C. No significant difference in the rate of degradation was observed.

Figure 17:
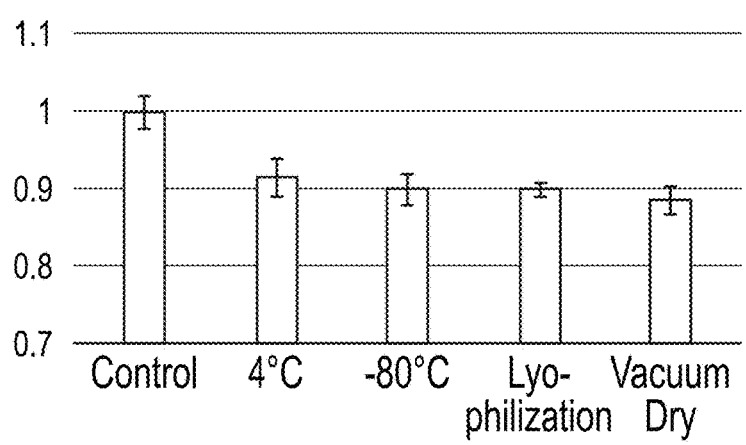
FIG. 17 is a graph depicting the mean diffusion time of BSA in the microspheres post storage at the specified conditions for period of 7 days as compared to control (freshly prepared hydrogel).

The diffusion times ($\tau_D$) of each storage condition were recorded by FCS and normalized based on the control gel, which was stored at room temperature. The values were then graphed and compared using statistical analysis (2-tailed t-test and standard deviation). FIG. 17 shows that the control gel had a significantly slower $\tau_D$ compared to the other storage conditions. There was slight, but not significantly different, variation in the $\tau_D$ values for the other storage conditions.

Minor differences in swelling ratio were found in the swelling ratio of the hydrogel microspheres stored at different conditions of storage as compared to RT control hydrogel microspheres. Surprisingly, the highest fold change of 1.31±0.24 was observed for hydrogel microspheres stored at −80° C. by slow freezing. The lowest fold change in swelling ratio was observed for samples pre-equilibrated with 10% DMSO and slow freezing at −80° C. and stored for 7 to 30 days. These results indicated that the hydrogel microspheres retained swelling ratio close to their initial swelling ratio. Measurement of swelling ratio of hydrogel gives a direct estimate of the water retention capacity of the hydrogel and is an indirect measurement of porosity or mesh size, crosslink density, and degradation of the swollen hydrogel network. Hydrogel microspheres of different conditions had close to their initial swelling ratio for both long and short term duration which indicated that the hydrogel microspheres were stable under the specified conditions of storage. This further implied maintenance of the hydrogel mesh size and crosslink density.

As with swelling ratio, no significant fold changes in hydrogel storage modulus post storage at specified conditions was observed when compared to control hydrogel microspheres. Significant difference in mechanical strength of the hydrogel microspheres stored at different conditions was also not observed. However, minor trends as observed for swelling ratio corresponded well with the mechanical strength. The mechanical strength of the hydrogels stored at −80° C. was lowest.

On examination of the stored microspheres by light microscopy, hydrogel microspheres were most affected by the lyophilization process and had a rough surface in comparison to RT controls as well as microspheres stored at other conditions. This was further confirmed by the examining the microstructure of the hydrogel microspheres by ESEM analysis which revealed presence of surface dips and pores in the lyophilized microspheres while absence of those in either the RT controls or the microspheres stored under different storage conditions. Changes in mechanical strength and swelling ratio of the lyophilized microspheres and hydrogels were not observed. Although lyophilization induced pore formation in the hydrogel microspheres, the pores were not sufficiently high in number to consistently affect the swelling or mechanical properties of the hydrogel microspheres or hydrogel.

As indicated by the results, no significant difference was found in the microsphere degradation times and size distribution after storage at any of the specified conditions for either 7 or 28 day.

The results indicated that diffusion times for BSA release from the hydrogels remained unchanged after storage under moist conditions or dry storage for 7 days and at temperatures of 2-4° C. or −20° C. The results further demonstrated that it is feasible to store the hydrogel microspheres along with the encapsulated protein at either temperature without loss in the physical properties or protein activity.

The methods of the present disclosure use Michael's type addition chemistry to create a time dependent hydrogel gelation to which an electric field is applied (electrospraying) to create microspheres, rather than to create PEG-based hydrogels that require bombardment with UV light for crosslinking, or the use of harsh chemical reactions. This advantage allows the microspheres of the present disclosure to be used for the delivery of an array of biologics (drugs, growth factors, enzymes, cells, etc.) without concern of damage to the deliverable. The tailorable nature of the process allows for the protection and subsequent controlled release of the deliverable of a range of time courses. The electrospraying method also allows for the production of small (~50 um) microspheres with a narrow size distribution, which cannot be achieved with other methods, except for microfluidics. However, microfluidic systems have a low-throughput (in comparison to electrospraying) and are not readily accessible for many laboratories.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of preparing hydrogel microspheres, the method comprising:
preparing a gel precursor solution, wherein the gel precursor solution comprises a polymer and crosslinker, the crosslinker comprising a thiol-terminated polymer, a cysteine-terminated oligopeptide, a cysteine-terminated polypeptide, and combinations thereof;
electrospraying the gel precursor solution into a collection medium, wherein the collection medium comprises mineral oil, olive oil, silicon oil, sunflower oil, canola oil, vegetable oil, palm oil, soybean oil, corn oil, rice bran oil, safflower oil, peanut oil, sesame oil, argan oil, grape seed oil, aqueous dextran solution, and combinations thereof, and wherein the gel precursor solution forms droplets in the collection medium;
collecting the droplets; and
allowing the collected droplets to gel by timed gelation in the collection medium to form hydro gel micro spheres.

2. The method of claim 1, wherein the polymer comprises an end group comprising an acrylate (Ac), a methacrylate, a vinyl sulfone (VS), an unsaturated double bond moiety, and combinations thereof.

3. The method of claim 2, wherein the polymer comprises polyethylene glycol (PEG), poly(glycolic acid) (PGA), poly(L-lactic acid) (PLA), poly(lactide-co-glycolide) (PLGA), poly(L-lactide) (PLLA), poly(D,L-lactide) (p(DLLA)), poly(ethylene glycol)1-co-poly(L-lactide) (PEG-PLLA), poly(ε-caprolactone) (PCL), poly(L-lactide-co-ε-caprolactone) (P(LLA-CL)), poly(ε-caprolactone-co-ethyl ethylene phosphate (P(CL-EEP)), poly(ethylene-co-vinyl alcohol), poly(ethylenimine), polymethylmethacrylate (PMMA), hyaluronic acid, chitosan, pluronics, polyacrylamide, poly(vinyl alcohol) (PVA), polyhydroxyethylmethacrylate (poly-HEMA), and combinations thereof.

4. The method of claim 1, wherein the crosslinker comprises dithioerthreitol (DTT), a polyethylene glycol thiol, a polyethylene glycol thioglacolate, a polyethylene glycol thiopropionate, glycol dimercaptoacetate (GDMA), glycol di(3-mercaptopropionate) (GDMP), glyceryl dithioglycolate (GDT), tris [2-(3-mercaptopropionyloxy)ethyl]isocyanurate, pentaerythritol tetra-3-mercaptopropionate, ethoxilated-trimethylolpropan tri-3-mercaptopropionate, 2,2'-(Ethylenedioxy) diethanethiol (EDDT), Tetraethylene glycol dithiol (TEGDT), (S)-2 aminobutane 1,4 dithiol (DTBA), a thiol terminated molecule, a cysteine containing oligo-peptide, a cysteine containing polypeptide, and combinations thereof.

5. The method of claim 1, wherein the gel precursor solution comprises a polymer concentration of about 3% w/v to about 40% w/v.

6. The method of claim 1, wherein the gel precursor solution comprises a pH of about 6 to about 8.5.

7. The method of claim 1, wherein an applied voltage comprises from about 1 kV to about 30 kV.

8. The method of claim 1, wherein an applied a flow rate comprises from about 0.5 ml hr$^{-1}$ to about 20 ml hr$^{-1}$.

9. The method of claim 1, wherein a tip to collector distance ranges from about 25 mm to about 300 mm.

10. The method of claim 1, wherein needle gauge ranges from about 30 G to about 14 G.

11. The method of claim 1, further comprising freezing the hydrogel microspheres.

12. The method of claim 11, further comprising rehydrating the hydrogel microspheres.

13. The method of claim 12, wherein the hydrogel microspheres are rehydrated in a solution comprising a biological molecule.

14. The method of claim 1, further comprising drying the hydrogel microspheres.

15. The method of claim 14, further comprising rehydrating the hydrogel microspheres.

16. The method of claim 15, wherein the hydrogel microspheres are rehydrated in a solution comprising a biological molecule.

17. The method of claim 1, wherein the gel precursor solution further comprises a biological molecule.

\* \* \* \* \*